(12) United States Patent
Schoenfeld et al.

(10) Patent No.: US 6,283,941 B1
(45) Date of Patent: Sep. 4, 2001

(54) SINGLE-USE SYRINGE WITH ASPIRATING MECHANISM

(75) Inventors: Joel Schoenfeld, Woodbury; David Shonfeld, Great Neck, both of NY (US)

(73) Assignee: Univec Inc., Farmingdale, NY (US)

(*) Notice: Subject to any disclaimer, the term of this patent is extended or adjusted under 35 U.S.C. 154(b) by 0 days.

(21) Appl. No.: 09/171,274

(22) PCT Filed: May 9, 1996

(86) PCT No.: PCT/US96/06597

§ 371 Date: Oct. 14, 1998

§ 102(e) Date: Oct. 14, 1998

(87) PCT Pub. No.: WO97/41903

PCT Pub. Date: Nov. 13, 1997

(Under 37 CFR 1.47)

Related U.S. Application Data

(63) Continuation-in-part of application No. 08/232,749, filed on Apr. 25, 1994, now Pat. No. 5,562,623, and a continuation-in-part of application No. 08/195,302, filed on Feb. 14, 1994, now Pat. No. 5,531,691.

(51) Int. Cl.[7] .................................................. A61M 5/00
(52) U.S. Cl. ........................................... 604/110; 604/209
(58) Field of Search ..................................... 604/110, 195, 604/218, 220, 263, 131, 181, 186, 187, 207, 208, 209, 210

(56) References Cited

U.S. PATENT DOCUMENTS

| 4,961,728 | 10/1990 | Kosinski . |
| 5,021,047 | * 6/1991 | Movern . |
| 5,328,476 | 7/1994 | Bidwell . |
| 5,527,285 | 6/1996 | Lenz et al. . |
| 5,531,691 | * 7/1996 | Shonfeld et al. . |
| 5,562,623 | * 10/1996 | Shonfeld et al. . |

* cited by examiner

*Primary Examiner*—Sharon Kennedy
*Assistant Examiner*—Catherine Serke
(74) *Attorney, Agent, or Firm*—Levisohn, Lerner, Berger & Langsam

(57) ABSTRACT

This invention is a single-use syringe (10) having a rd-like plunger (14) and made with a plurality of frusto-conical or bead-like ratchet teeth (28). A radially resilient, spring locking clip (40) dangles on the ratchet portion of the plunger. The location of the clip determines the maximum dosage which can be administered by the syringe. Aspirating gaps (114) can be provided on the plunger rod to allow selective aspiration prior to loading and dispensing medication. In use, a first withdrawal of the plunger with respect to the barrel (12) allows, for aspiration, then medication can be drawn into the cavity of the barrel since the cam tooth (83) of the locking spring clip glides, by radial flexing, over the surface of the ratchet teeth and, yet, the locking spring is maintained in relative position along the barrel by outwardly directed contact points embedding into the interior sidewall of the barrel.

19 Claims, 19 Drawing Sheets

SINGLE-USE SYRINGE WITH ASPIRATING MECHANISM

This Application is a 371 of PCT/US96/06597 filed May 9, 1996.

RELATED APPLICATIONS

This is a continuation-in-part application of application Ser. No. 08/195,302, filed Feb. 14, 1994, now U.S. Pat. No. 5,531,691 entitled Single-Use Syringe Assembly and application Ser. No. 08/232,749 filed Apr. 25, 1994 now U.S. Pat. No. 5,562,623 also entitled Single-Use Syringe Assembly Comprising Spring Clip Lock and Plunger. Both of the applications are incorporated herein by reference as if fully presented.

BACKGROUND OF THE INVENTION AND DESCRIPTION OF THE PRIOR ART

This invention relates generally to hypodermic needles and syringes, and more particularly the invention relates to a spring locking clip and associated plunger which can be used to convert a plastic hypodermic syringe barrel into a single-use, difficult to reuse, inexpensive syringe made of already medically approved material. For the purposes of this invention the term single-use means that the full maximum dosage placed into the syringe can only be administered one-time. The syringe, however, can administer medication multiple times, each time, however, delivering only a portion of the full medication capable of being drawn into the syringe by a single, full proximal drawing of the plunger rod with respect to the syringe barrel. For short hand notation, the term single-use means a single full dispensing of the entirety of medication drawn into the barrel and includes one or more possible uses, with each use delivering less dosage than the maximum. The cumulative total of delivered dosages obtained by all uses can not exceed the maximum or full dosage drawn into the syringe by a single rearward reciprocation of the plunger rod with respect to the barrel. The syringe is a one-time use syringe when the maximum or full dosage of the syringe (determined by the barrel capacity and/or the position of the spring clip on the plunger) is fully administered in a first and only usage. If that occurs, the spring clip is moved to its full distal position and all reuses are blocked. Where less than the maximum dosage is drawn into the barrel is delivered on the first or succeeding dosage deliveries, the succeeding dosages administered are necessarily less than the maximum. There can be only one full distal movement of the plunger rod, to administer medication made up of individual administrations of medication. The sum of all medication dispensed cannot exceed a single dosage capacity of the barrel of the syringe. In this manner, the device is a "single-use" syringe.

The safe, one-time use and subsequent disposal of hypodermic needles and syringes are immediate concerns in the medical and health professions. Accidental needle stick injuries following use of a syringe pose a significant risk to patients, physicians and nurses. The risk is a source of great anxiety due to the current HIV and hepatitis infection concerns of the general public. Thus, extreme care must be taken in the safe handling and disposal of used needles and syringes. Toward this end, the present invention represents a single-use needle and syringe assembly. After the needle and syringe (hereinafter collectively referred to as the syringe) are used once, the mechanism of the present invention precludes further uses. It will, therefore, be more likely properly discarded than if further use were possible. The possibility of patient to patient cross contamination and drug user to drug user cross contamination are reduced.

The present invention is compact and, therefore, is capable of being implemented into syringes of extremely small size barrel capacity, including syringes capable of administering dosages as low as 0.1 cc. The prior art, on the other hand, as will be more fully explained hereinafter, cannot be easily and/or economically downsized while maintaining the effectiveness of the one-time use only mechanism they describe and, therefore, they have not been commercially introduced in sizes smaller than standard 3 cc syringe bodies. The initial axial location of the locking mechanism with reference to the syringe barrel of the prior art single-use syringes, was the means for limiting a 3 cc conventional syringe to a maximum 1 cc dosage. However, it is clearly desired to have smaller maximum dosage syringes where the size of the syringe, not only the location of the clip, determines the maximum dosage capacity. It should be appreciated, however, that the present invention can also be adapted for use with 3 cc or other maximum dosage syringe barrels and, yet, the present invention has particular applicability to syringes of low dosage barrel capacity even those as low as 0.1 cc capacity.

It is generally recognized that a low cost syringe is essential to meet the needs of less developed countries and to contribute to the reduction of health costs worldwide. A low cost would mitigate syringe re-use now encountered with disposable syringes. The cross contamination resulting from patient to patient reuse of the same syringe would be obviated by a single-use only syringe. It would also reduce patient anxiety resulting from suspected potential infection from prior syringe use.

The present invention provides a simple and inexpensive mechanism for limiting the usage of a syringe (with or without needle) to one-time or single-use only. The syringe is intended to be assembled at the manufacturing facility and provided to the physician (or nurse, patient, etc.) for use. The user fills the syringe with the appropriate medication in the conventional manner, i.e., by withdrawing the plunger with respect to the cylindrical barrel of the syringe, thereby drawing medication through the needle tip and into the chamber of the barrel. According to the present invention, the plunger can be repeatedly reciprocated, for aspirating, prior to loading with medication. Once the user makes the decision that the amount of aspirating reciprocations have been sufficient, a positive movement of the plunger with respect to the barrel ensures the operation of the single-use locking mechanism. Then, again, using conventional technique, the needle is inserted to pierce the patient's skin. The plunger is manually moved with respect to the cylindrical barrel thereby forcing a piston toward the distal end of the syringe. The piston forces the medication out through the needle tip.

During the dosage administration portion of the procedure, according to the present invention, as will be more fully explained hereinafter, a locking spring clip travels along with the plunger shaft and, when it reaches the distal position, locking or contact points are held against the interior sidewall of the cylindrical barrel with the piston abutting the base of the locking spring clip. A second attempted retraction of the plunger with respect to the cylindrical barrel of the syringe is blocked. Thus, no further medication can be pulled into the syringe and, therefore, the syringe is incapable of being used a second time. A simple, inexpensive single-use syringe is provided. The locking mechanism, precluding reuse, is automatic, ire., it operates to block reuse, after aspiration, without a conscious operation by the user to engage its operation.

The design of an economically producible syringe assembly having the feature of single-use and whose safety or one-time use operation is difficult to defeat has been the subject of numerous patents and efforts. Such a syringe should be easy to manufacture and assemble, function in a standard manner, be able to deliver different volumes of fluid, utilize materials which are universally approved for medical use, preferably require standard equipment to manufacture such as used for making syringes in current use, and, importantly, be low in cost.

The present invention accomplishes the above objects by utilizing a new and unique plunger in association and in combination with a new and unique spring locking clip. The plunger comprises a plurality of cylindrical i.e., frusto-conical ratchet teeth or in an alternate embodiment, beads. The spring clip is located by the manufacturer at a particular location along the axis of the plunger so as to limit maximum withdrawal of the plunger, hence dosage of the syringe. According to the preferred embodiment of the present invention, longitudinal spacing is provided between at least two of the ratchet teeth or heads. This allows for plunger withdrawal and advancement without associated spring clip advancement. This, then, allows for aspirating the syringe, prior to loading of the barrel with medication. Also, the use of bead-shaped ratchet teeth, in lieu of our prior disclosed frusto-conical, ratchet teeth, allows for smoother operational motion during plunger withdrawal and a greatly reduced force, during plunger withdrawal, as compared to the withdrawal force of the plunger when the ratchet teeth are cone-shaped or frusto-conical, as in our prior devices.

Currently, there is a specification for the maximum withdrawal force of a plunger in a hypodermic needle/syringe. This was established by the International Standards Organization. Our single-use syringe designs, the subject of parent patent application Ser. Nos. 08/195,302, filed Feb. 14, 1994, and 08/232,749, filed Apr. 25, 1994, were tested and, in some units, found to slightly exceed the specification, although the majority of units had the plunger withdrawal force below the maximum limit of the standard. So as to ensure a high quality product which always satisfies the standard, the present invention was developed. As an alternative, of course, a new standard maximum plunger withdrawal force could be established for single use syringes, since the present "standard" covers disposable syringes which are intended to be and can be repeatedly used.

According to the preferred version of the present invention, the ratchet teeth of the plunger are "bead shaped." The spring clip, then, as the plunger rod is withdrawn, does not, in contrast to our device shown in our prior patent applications, follow each ratchet tooth discontinuity. Rather, the beads allow the spring clip to more smoothly glide over the surface of the beads. The force of withdrawal is reduced and found to be nearly the same as for a reusable syringe and a plunger not having a spring locking clip.

A multiply aspiratable syringe with a spring locking clip is desirable. The invention disclosed in the prior patent applications was not designed to allow for multiple aspirations (i.e., multiple reciprocations of the plunger to draw air into and then expel it from the barrel) but to a limited extent aspiration was possible in those situations where the initial withdrawal and projection of the plunger advanced the spring clip to a position less than the full distal or forward position.

The present invention is intended to allow for multiple aspirations. The device uses a gap between ratchet teeth so that any movement of the plunger, when the spring clip is between ratchet teeth, i.e., within the gap, does not cause the spring locking clip to advance. Of course, the amount of gap between ratchet teeth determines the amount of aspirating.

The use of this new plunger and spring locking clip blocks reuse of the syringe. The construction can be incorporated into syringes of even 0.1 cc barrel size, without any loss of efficiency or safety. The operating mechanism of the present invention allows extremely small volumetric capacity of syringes to be manufactured, without loss of performance. In contrast, the locking mechanisms of prior art single-use syringes operate by use of different mechanisms and, therefore, very small volume syringes cannot be manufactured. The present invention is economical to manufacture, has tamper-proof features, administers medication using conventional techniques, is made of medically approved materials, and can be made with standard equipment.

The present invention has the withdrawal force of the plunger within acceptable limits of multiple-use syringes and, yet, is a single-use syringe. The mechanical withdrawal of the plunger having bead-like teeth is a smoother operation than that which is present with frusto-conical ratchet teeth. Also, the use of one or more aspirating gaps, between ratchet teeth, allows the syringe to be selectively and repeatedly aspirating.

It is a feature of the present invention to provide the thumb-contacting portion of the syringe plunger as a break-apart disc such that, after use, the user of the syringe can simply bend or twist and remove the thumb-contacting disc and, thereby, further disable the syringe from a subsequent reuse. The ease of removal of the thumb-contacting portion of the plunger shaft from the syringe also serves as a means for tracking inventory of the syringes.

DESCRIPTION OF THE PRIOR ART

The various approaches described in the patent literature and in other publications have generally described mechanisms for providing single-use syringes, without reference to geometric limitations such as the minimum total volume such a syringe barrel can contain. It is clear that some minimum contained volume limit exists for single-use syringes which depend not only on the design, but also on limitations on produceability resulting from small dimensions. It is the present practice, where small quantities of medication are to be injected, to prefer the use of syringes of reduced total volume rather than limiting the motion of a larger barrel capacity device as both the accuracy and ease of use are thereby enhanced. The present invention, in contrast to the prior art, uses an entirely different mechanism and operating force to block syringe reuse. Construction of syringes of extremely small volumetric capacity can thus be achieved.

Safety syringes have been made, in the past, which provide some degree of protection against accidental needle injury. The designs require relatively complex mechanisms or are relatively bulky. Often, they have been relatively expensive to manufacture. Most of the prior art single-use limiting mechanisms are intended for use with the standard X-shaped plunger of conventional syringes. The present invention, on the other hand, contemplates the use of an entirely new plunger which is, in basic form, a rod comprised of ratchet teeth, preferably bead-like teeth. Moreover, activation of the safety features of the prior art mechanisms can sometimes fail or be intentionally disengaged. It is believed that the present invention is more effective at preventing syringe reuse.

Of particular importance, however, as mentioned, the present invention is believed extremely efficient, inexpensive and capable of being incorporated into syringes of dimensions suitable for even 0.1 cc maximum dosage capacity. In this manner, the device can be incorporated into very small dosage syringes. This is highly desirable. In contrast, prior art single-use or "safety" syringes seem incapable or difficult to reduce down in size. They have not been commercialized in 0.1 cc maximum dose capacity but, rather, the manufacturers use standard larger barrel syringes (3 cc, for example) and limit the degree of movement of the plunger shaft to limit the maximum dosage. It is a specific object of the present invention to provide a single-use syringe in a maximum capacity as low as 0.1 cc which is primarily accomplished by downsizing of the barrel, not by location of the spring locking clip.

Previous approaches to the design of single-use disposable plastic syringes may be classified as follows:

(a) Locking of the plunger after delivery;
(b) Disengagement of the plunger;
(c) Withdrawal of the needle into the syringe barrel after dose delivery;
(d) Physical destruction of some portion of the syringe;
(e) Chemical means to disable the syringe after first use; and
(f) The use of supplementary means such as sleeves to prevent reuse of the syringe while simultaneously offering needle-stick protection.

A syringe of the present invention utilizes a mechanical method to lock the plunger from further use by a novel spring locking clip mechanism, as described below.

Prior art locking mechanisms generally operated on conventional X-shaped plungers, and, in some cases, on a cylindrical plunger. In use of the X-shaped plunger, the plunger is maintained in axial alignment with the axis of the barrel by the edges of the x-shape of the plunger. In use of a locking device on a cylindrical plunger, the locking devices were symmetrical, extending entirely around the plunger. Thus, these plungers were maintained in axial alignment with the barrel. The axial alignment between barrel and plunger, in the prior art X-shaped and locking clip devices and those cylindrical plungers with surrounding locking clips, precluded the potentially desired reduction of the maximum volume capacity of the syringe.

The present invention, in contrast, uses a new locking mechanism on a basically cylindrical plunger. The structure and manner of operation of the present inventive spring locking clip results in a radial displacement of the axis of the plunger within the barrel. This non-axial alignment between plunger and barrel allows for the manufacture of single-use syringes in much smaller volumetric capacity than previously available.

U.S. Pat. No. 4,386,606 utilizes sharp edges on a plunger, cam or barrel to securely lock the syringe having an X-shaped plunger.

U.S. Pat. No. 4,367,738 describes a non-reusable syringe utilizing a plurality of stiff, flexible spikes.

U.S. Pat. No. 4,731,068 shows rigidly secured spider-like barbs mounted on a cylindrical plunger to lock the syringe after delivery to prevent reuse.

U.S. Pat. No. 4,952,206 uses barbs to allow a washer located within a valve to impede fluid flow after drug delivery.

U.S. Pat. No. 4,961,728 utilizes non-parallel barbs on a locking element for an X-shaped plunger.

U.S. Pat. No. 4,979,943 provides a reversible stop member which permits plunger motion in one direction only.

U.S. Pat. No. 5,000,737 utilizes a circular or fluted, barbed lock which engages an X-shaped plunger.

U.S. Pat. No. 5,021,047 and U.S. Pat. No. 5,138,466 utilize locking barbs which completely surround the plunger. The motion of the lock as it relates to the plunger causes it to flex in an axial mode as it is forced over the ratchet teeth.

U.S. Pat. No. 5,205,825 utilizes an insertable clip to lock X-shaped plungers.

WO 89/00432 utilizes a ratchet plunger and ratchet wall to prevent reuse.

U.S. Pat. No. 5,000,737 relates to a single-use disposable syringe. The drawings reveal a device adapted for placement over X-shaped conventional plunger shafts. Outwardly directed points of the claimed flute are intended to dig into the interior cylindrical sidewall or surface of the barrel so as to prevent movement of the disk with respect to the barrel when the plunger shaft is moved in the proximal direction (the direction for drawing medication into the barrel). Inwardly directed edges are adapted to engage the adjacent walls of the X-shaped plunger so that the device travels along with the plunger when the plunger is moved distally (to dispense the medication). FIGS. 8–16 of the identified patent relate to the claimed invention of the '737 patent. That device is intended to be held in a quadrant of the syringe barrel defined by the X-shaped plunger member. It is described, according to the patent, as "elongated" i.e., its length is greater than its width dimension.

The spring locking clip of the present invention, on the other hand, as will be more fully explained, is not elongated. It is compact and easily fabricated for small-sized syringes. It is less expensive to manufacture and believed far simpler to fabricate. It will not fail in the event of axial misalignment and, indeed, efficiently operates by axial nonalignment. By being constructed and operated in this manner, the volume of the syringe can be made far smaller than that capable of construction with prior art syringes. Furthermore, the present invention contemplates use in connection with a new plunger. The spring locking clip as now presented is not confined within a quadrant of the barrel, defined by an X-shaped plunger, but, rather, it extends only partially around a new, basically cylindrical plunger located within the barrel. This provides more uniform pressure of the locking mechanism against the interior sidewall of the barrel and ensures that the present invention is useful in preventing reuse of a one-time used syringe. The manner of operating, i.e., the plunger being pushed off-center or out of axial alignment with respect to the axis of the syringe barrel has vast advantages over the prior art. The '737 patent also shows a disc-like member which operates in a manner quite similar to the flute claimed in the '737 patent. It, too, is intended for use with conventional X-shaped plungers. It, too, seems difficult to downsize for manufacture of 0.1 cc syringes.

U.S. Pat. No. 5,151,088 also relates to a safety needle and syringe assembly. A disposable syringe and needle assembly is depicted and described having a small, rigid, retractable needle shield provided in the syringe. Following an injection, the needle shield is extended into a locked position covering the needle. The shield only assumes the locked position when the user presses the syringe plunger past the zero volume point. Thus, if the user does not accidentally or consciously do so, this device will not block reuse. It is an object of the present invention to automatically prevent reuse of a syringe after aspirating, so as to eliminate person to person contamination, a consequence of needle reuse. Automatic engagement of the locking mechanism is not accomplished by the '088 device. Utilizing the invention of the '088 patent, a user, desiring to defeat the mechanism and to reuse the syringe, can avoid engagement of the locking mechanism by deliberately failing to press the syringe plunger past the zero volume point.

U.S. Pat. No. 5,205,825 (Allison et al.) relates to an insertable element for preventing reuse of plastic syringes. This device, similar to that shown in the Free et. al. '737 patent, provides a locking mechanism intended to be retrofitted into existing conventional syringes by inserting the device onto the standard X-shaped plunger within a plastic cylindrical barrel of the syringe. The same comments previously made with respect to the device of the Free et. al. patent are equally applicable to the Allison et. al. patent i.e., with respect to its inability to be made effectively and efficiently in a smaller maximum dose size and, further, the advantages achieved by the present invention, a consequence of the intended nonalignment of the plunger with the axis of the cylindrical barrel.

U.S. Pat. No. 5,067,942 relates to a single-use hypodermic needle, as well. When the needle assembly and the syringe are assembled, two separable tabs held within a basket force the sheath to retract and expose the port in the needle whereby a fluid can flow through the needle. Upon disassembly of the needle syringe, the tabs separate from the basket and are effectively destroyed for further use in retracting the sheath. The present invention is believed far simpler, less expensive to manufacture, more automatic and is more easily adapted for smaller sized syringes than that shown in the '942 patent.

A number of safety syringe designs incorporating needle covers have also been proposed. U.S. Pat. Nos. 4,909,791 and 4,982,842 employ jaw members pivotally mounted onto a syringe barrel for covering a needle after use.

U.S. Pat. No. 4,969,877 discloses a syringe assembly in which an outer casing is provided around an inner chamber or syringe portion which slides on the outer casing to an operational position and to a retracted position at the forward and rearward ends of the outer casing, respectively.

U.S. Pat. No. 4,013,073 discloses a collapsible single-use syringe wherein the interior of the collapsible wall is constructed such that when the walls are pressed together to discharge the medication, they interlock and therefore render the device incapable for reuse.

U.S. Pat. No. 4,022,206 shows a method and apparatus for storing and delivering a vaccine in a single dose prepackaged system. No provision is made for rendering the unit mechanically inoperable for subsequent use.

U.S. Pat. No. 4,391,273 shows a rigid type syringe including a pin which is attached to the piston which penetrates the bottom wall of the cylinder after the injection has been completed. This, too, renders the syringe inoperable after a first time use. In an alternative embodiment, the patent shows a knife blade which permits movement of the cylinder in a forward direction but the knife serves to cut the sidewall of the cylinder if there is an attempt to recycle the piston or reuse the syringe.

Prior techniques for preventing reuse of syringes include various arrangements for locking out the plunger of the syringe after it has been first loaded and then reciprocated to the end of its travel to inject the contents of the syringe. For example, U.S. Pat. No. 4,731,068 discloses a two-part lock construction having a band or sleeve assembled at the injection end of the syringe and dimensioned to be frictionally slidable along the inner wall of the syringe. A spider-like element is mounted in a fixed position on the plunger and has barbed points engaged with the sleeve. When the plunger is first retracted, the spider element and sleeve travel toward the end of the syringe, together with the plunger. When the plunger is depressed toward the injection end, the sleeve remains at the distal end (through frictional engagement with the inner wall) while the spider element travels toward the injection end with the plunger. If a second attempt is made to retract the plunger, the barbs of the spider element, now exposed to the inner wall in the absence of the sleeve, will engage the inner wall of the syringe and prevent a second retraction.

An alternative embodiment shown in the '068 patent has the sleeve slidably supported on the plunger and engaged with the spider element. That element is provided with curved spring-like prongs assembled at the distal end of the syringe. On the first retraction, the sleeve remains engaged with the spider element, and on the first depression, it is moved toward the injection end to expose the prongs of the spider element. An attempt to retract the plunger a second time will be prevented by engagement of the prongs with the plunger. Other devices, for example, U.S. Pat. Nos. 4,781,684; 4,493,703; 4,391,272 and 4,367,738 provide modifications to the plunger or syringe wall structure. These allow only one way movement of the plunger or lock or disable the plunger after a first depression. They, too, relate to single use syringes.

U.S. Pat. No. 5,290,235 relates to a non-reusable syringe. In use, a locking member interacts with the guide arrangement of the plunger and the inside surface of the hollow body of the syringe so as to allow a first intake stroke and a delivery stroke but to prevent a second intake stroke of the plunger.

The device shown in the '235 patent generally comprises a conventional syringe with hollow body; an elonged plunger rod extending out of the body for facilitating movement of a piston; the plunger rod having a guide means carrying a locking member, like a plate, with at least one snag projection facing the inside surface of the barrel wherein the guide causes relative pivotal movement of the locking member from a first position where the plunger freely moves in the distal direction to a second position wherein the barb(s) engage the inside wall of the barrel.

The construction of the device of the '235 patent is far more complicated than that of the present invention. The present invention contemplates the use of a simply molded, basically cylindrical, yet ratcheted, plunger shaft, having a spring clip mounted thereon. The original location of the spring clip will determine the maximum volume of the supplied liquid. The device of the '235 patent, in contrast, shows a complicated plunger. It does not seem suitable for mass production. The present invention allows a single plunger rod to be used for a variety of maximum dosage syringes. In the '235 patent, each syringe with a different desired maximum capacity requires a different distance on the plunger between the first face 22 and the stop face 26.

The present invention is extremely easy to fabricate, manufacture and assemble. It is easily capable of use with standard size syringe barrels and, in addition, of commercial importance, it is fully capable of being down-sized for use in connection with syringes having a maximum dosage capacity as low as 0.1 cc. The present invention is fail-safe, i.e., substantially automatic in operation and, in the preferred embodiment, as will be more fully explained, provides multiple lock-out mechanisms thereby ensuring that re-use of a one-time used syringe can not occur. The present invention allows for the selective axial location of the spring locking chip on the cylindrical plunger shaft such that maximum dosages can be provided by the manufacturer even though the syringe barrel and plunger can be manufactured in a single size. Thus, location of the locking spring mechanism with respect to the barrel and the plunger, at the time of manufacture, ensures that the administering physician, nurse, technician or user can not administer an overdose of the particular medication. The spring locking clip mechanism can assume a variety of initial locations at the time of manufacture depending upon location on the plunger, so that there can be economy of manufacture, since only one cylindrical barrel and plunger element need be manufactured. The position of original location of the spring locking clip or mechanism with respect to the plunger determines the maximum quantity of dosage which a particular syringe is capable of administering. Thus, the present invention not only provides a mechanism for ensuring that syringes can not be reused, but, in addition, the spring locking clip mechanism limits the amount of medication which can be administered for any particular use of that syringe.

The present invention, as will be more fully detailed hereinafter, also provides for a back-up safety mechanism to further disable the syringe after its first time use. This feature however, is not automatic but, rather, requires that the user physically separate the thumb contacting disc portion of the plunger from the plunger shaft to thereby further mechanically disable the syringe from being used a second time. Removal of the thumb-contacting disc portion serves a secondary purpose of facilitating inventory control since the discs, the remaining portion of the syringe after the bulk has been discarded, can be used to facilitate inventory control.

It is a further object of the present invention to provide yet another lock-out feature preventing the syringe from being used a second time. In this embodiment, a full distal reciprocation of the plunger with respect to the syringe barrel will cause an annular male dove-tail portion of the thumb-contacting disc to engage and mechanically lock into an annular female dove-tail like arrangement of the cylindrical barrel. This locks the disc and shaft fully within the interior of the barrel and prevents movement of the shaft outwardly with respect to the barrel. Blockage of this movement prevents further medication from being withdrawn into the body of the syringe, thereby rendering the device non-reusable.

The geometry of the present invention allows the device to be made in maximum dosages as low as 0.1 cc. This is due to the fact, as will be explained, that the locking device operates radially, i.e., it pushes the plunger rod off axis in the barrel. In this manner of operation, the locking clip need only be a single thickness. It need not surround the plunger rod. As constructed and in operation, the plunger rod, barrel and locking clip can be downsized without loss of function, to a size to deliver medication as low as 0.1 cc maximum barrel dosage. This is not available in the prior art.

SUMMARY OF THE INVENTION

The present invention relates to a single-use syringe wherein reuse is mechanically blocked. It is an object of the present invention to provide a single-use syringe which is simple in construction, inexpensive to manufacture and automatically prevents re-use. It is a further object of the present invention to provide an inexpensive syringe which is capable of mechanically blocking re-use, which syringe can be made of very small dosage capacity. For example, it is a specific object of the present invention to provide a one-time use syringe capable of maximum dosage as low as 0.1 cc.

It is a further object of the present invention to provide a single use syringe which has a smooth mechanical operation and a plunger retraction force less than the industry maximum standard.

It is a further object of the present invention to provide a single use syringe which can be selectively and repeatedly aspirated prior to medication being withdrawn into the barrel.

Another object of the present invention is to provide an inexpensive, spring-like mechanism which, when placed upon a ratcheted plunger shaft, limits the quantity of medication which can be withdrawn into the barrel of the syringe and then administered. The initial location of the spring locking mechanism, with respect to the ratcheted cylindrical shaft, determines the maximum capacity of that particular syringe. Thus, it is a specific object of the present invention to provide a single-use syringe capable of having a variety of maximum dosage capacities dependent upon the initial axial location of the spring locking clip with respect to the plunger shaft. The manufacture of a single size barrel, therefore, provides for economies of manufacture.

It is a further object of the present invention to ensure that a one-time use syringe is provided which can not be easily intentionally disabled. It is also an object of the invention to ensure a one time use syringe which is intended to operate by radial displacement between the plunger and the axis of the barrel of the syringe. This is, in part, accomplished by the use of a new plunger shaft which is basically rod-like, not x-shaped, and by use of a spring-like locking clip which radially flexes inwardly and outwardly, locatable on the plunger shaft. Non-axial alignment between the cylindrical plunger shaft and the inside barrel wall of the syringe enables the one-time use locking mechanism to be downsized for syringes capable of providing dosages as low as 0.1 cc. It is a specific object of the present invention to provide a one-time use locking mechanism for a disposable syringe which is capable of use on cylindrical plunger shafts. Eliminating the X-shaped plunger allows the present invention to be more easily made in smaller dimensions. Using the ratcheted, plunger rod and the spring locking clip of the present invention eliminates the necessity shown in the prior art, of locking clips substantially surrounding cylindrical plunger shafts. In this manner, very small capacity syringes can be made.

The plunger shaft of the present invention further comprises, in the preferred embodiment a plurality of bead-like ratchet teeth. The spring locking clip, as will be explained, is intended to be initially located on a selected one tooth or bead of the plunger. Thus, the present invention allows for more precise dosage limiting than available with the prior art devices. A mechanical locking between the spring locking clip and the plunger ensures the maximum dosage is administered in fixed integral amounts whereas the prior art controls maximum dosage by infinitely variable sliding location of a flute along the X-shaped legs of the plunger, not nearly as easy to precisely control.

It is a further object of the present invention to provide a thumb contacting disc portion of the plunger shaft which can be selectively bent or twisted and removed from the plunger shaft after the syringe has been used. In this manner, the thumb-contacting disc portion can be used for keeping track of syringe usage and inventory. Furthermore, removal of the thumb-contacting disc portion of the plunger shaft serves to further disable the syringe, preventing easy reuse.

It is a further object of the present invention to provide another locking mechanism further disabling the syringe from re-use after a one-time intended use. This locking mechanism is accomplished by cooperation of an annular male dove-tail of the thumb-contacting disc portion of the plunger shaft with an annular female dove-tail-like receptacle portion at the proximal end of the barrel of the syringe. A full reciprocating cycle of the plunger shaft with respect to the cylindrical barrel of the syringe serves to mechanically lock the plunger shaft into its full distal position thereby preventing a second withdrawal of the plunger shaft with respect to the barrel of the syringe.

Another object of the present invention is to provide a mechanism whereby syringes of identical dimensions can be restricted to contain and deliver different dosages, thereby reducing the need for syringes of different sizes.

The present invention is directed to a mechanical means which utilizes a ratchet plunger and spring locking clip to achieve the above enumerated desirable features. The operation of the syringe assembly relies on a loosely engaging spring locking clip which allows the syringe to be aspirated, as desired, and filled with medication, when the plunger is withdrawn. This clip is nearly semi-cylindrical, and has the ability to flex radially, both inwardly and outwardly, and contains barbs outwardly directed so as to be able to position themselves sufficiently independently to conform to variations in barrel diameter due to manufacturing tolerances or imperfections. The present invention also has alignment elements, which function as the locking clip advances toward the needle. The alignment elements add stability when the plunger is attempted to be reused for a second refill as described below. The plunger contains a front seal to provide smooth functioning by applying a uniformly distributed force on the embedding barbs during any attempted second withdrawal of the plunger after a first medication delivery.

According to the preferred embodiment of the present invention, a gap is provided between adjacent ratchet teeth. The gap allows the plunger to be partially withdrawn for aspirating. Then, after aspirating, the plunger is withdrawn to fill the syringe, the spring locking clip, although stationary in the syringe barrel, being forced to cam over one or more teeth of the ratcheted cylindrical plunger as a result of radial flexing. The clip can accommodate the varying diameter of each tooth of the plunger because it is radially open, being only about semi-cylindrical in shape. During delivery of fluid by the forward relative motion of the plunger and piston, the clip flexes radially. The clip is carried or urged forward relative to the barrel by the plunger. After injection, with the plunger at its most forward position, the clip prevents any second rearward withdrawal of the plunger since the barbs are embedded into the plastic barrel wall. Any attempt to overcome the resulting friction results in the plunger rod breaking because its tensile strength, reduced by a reduced cross section of the plunger at predetermined locations, is less than the force necessary to overcome the frictional resistance provided by the barbs embedded in the inside wall of the barrel. In other embodiments, a second or more reduced diameter sections of the plunger can be provided to further protect against reuse.

In alternative embodiments, a single plunger rod can be provided with multiple gaps between adjacent ratchet teeth. This allows the syringe to be used a fixed number of times, with selective aspirating.

It is an object of the present invention to provide a design which is readily manufacturable by standard molding and assembly methodology at a cost comparable to that currently experienced in the manufacture of disposable plastic syringes.

It is an object of the present invention to achieve smooth operation of the syringe. The bead-like ratchet teeth provide smooth operation and a retracting force of the plunger from the barrel less than the maximum demanded of industry standards. It is an object of the invention to provide a one-time use syringe which will not jam, particularly for lower volume syringe sizes.

It is a further aim to provide a plunger and spring locking clip in which the mechanism allowing positioning and actuation of the lock function is a consequence of radial flexing of the locking member around the plunger and within the barrel of the syringe.

It is a further object to provide a spring locking clip having flexible, locking or contact points capable of independently interacting with the barrel wall and allowing for variations in barrel diameter.

It is a further object to provide a syringe wherein attempted re-use leads to rendering the syringe inoperable.

It is a further aim to provide secondary fail-safe mechanisms, i.e., complimentary means to provide tamper-proof capability.

It is a further object of the present invention to provide a design offering the above features for syringes capable of precisely delivering as little as 0.1 cc of liquid.

It is an object to provide the above features within a single syringe having a variable predetermined maximum volume of fluid which can be withdrawn into the syringe.

It is an object of the present invention to achieve the above desired aims utilizing materials which have been approved by official and government regulations.

It is an object of the present invention to allow the syringe to be able to be modified to minimize accidental needle pricks.

It is an object of the present invention to provide a single-use syringe which can be aspirated one or more times at the same or different quantities of aspiration prior to filling with medication.

It is also an object of the present invention to provide for multiple lock mechanisms to assure syringe disablement by different approaches and to hinder access to the operative locking mechanisms.

It is an object of the present invention to allow varying amounts of fluid and selected multiple uses to be deliverable with a given barrel diameter.

The objects, features and advantages of the present invention will become apparent from the following detailed description of the preferred embodiment of the invention considered in conjunction with the drawings, as follows:

DETAILED DESCRIPTION OF THE DRAWINGS AND THE PREFERRED EMBODIMENT

Figure 1:
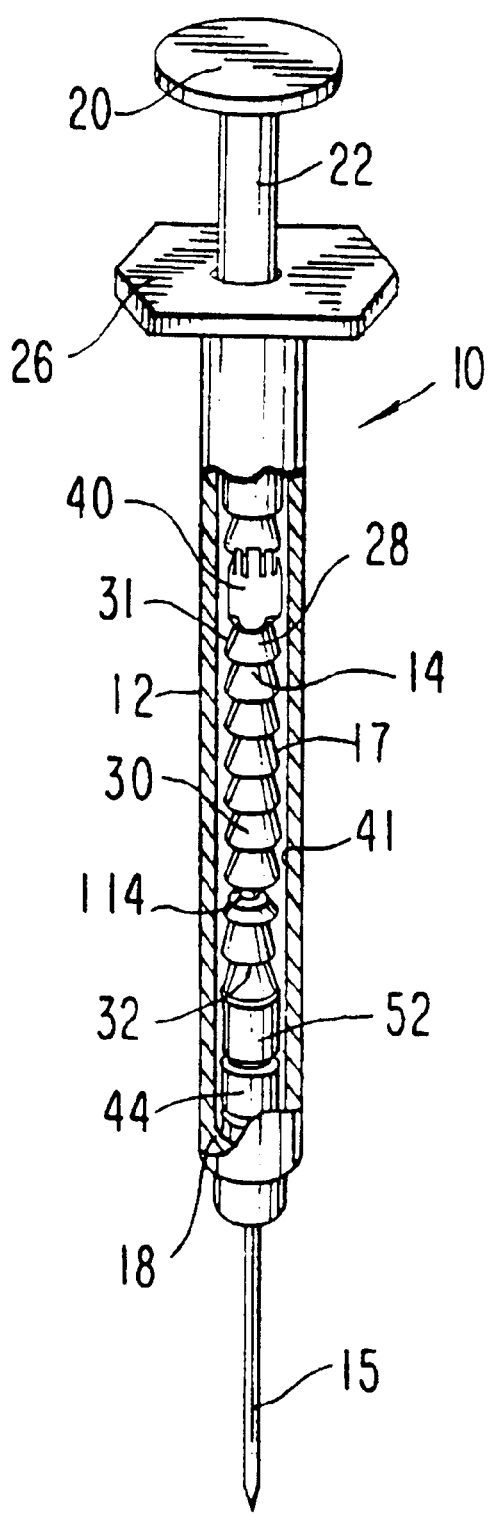
FIG. 1 is a perspective side view of the syringe portion of the present invention showing the spring locking clip in its initial position, as sold by a manufacturer, dangling on the ratcheted plunger shaft. This Figure shows the syringe of the present invention in its configuration as intended to be distributed to a user for first filling with medication and then subsequent dispensing of the same. The needle extending from the syringe is conventional in configuration.
Figure 2:
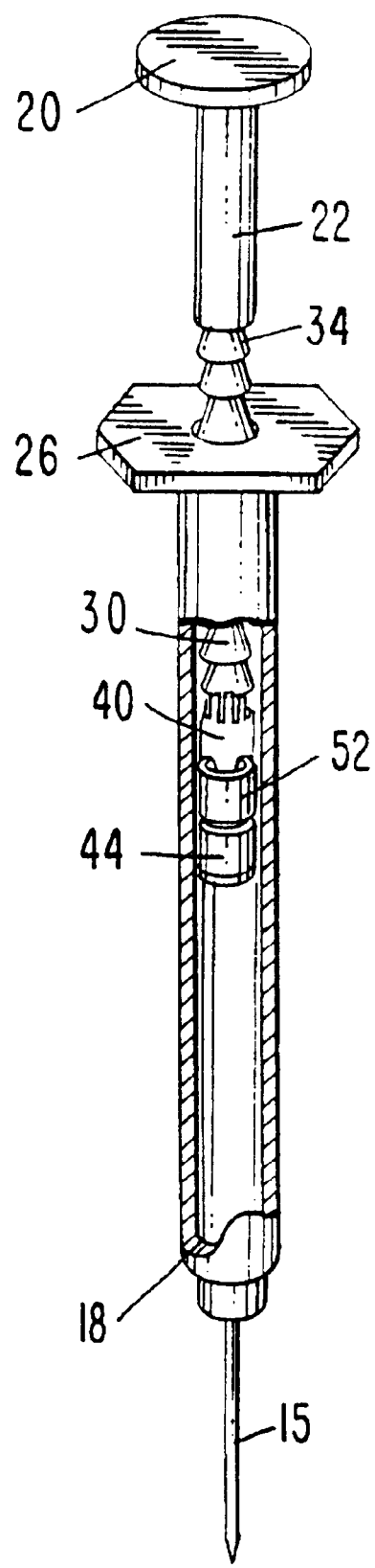
FIG. 2 is a perspective side view of the present invention, in its position after being filled with medication and ready to be dispensed.
Figure 3:
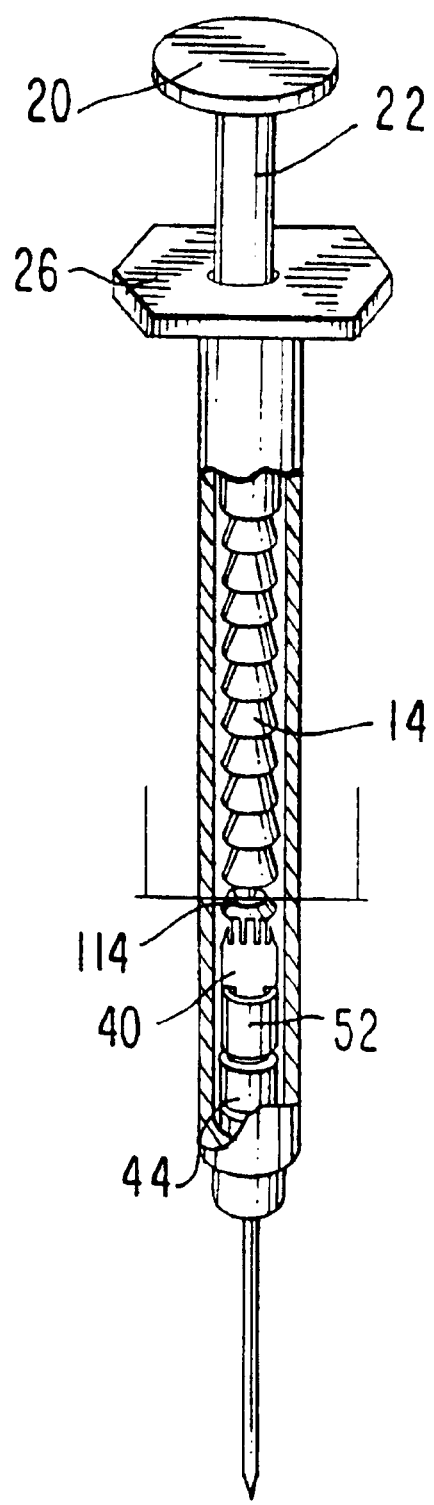
FIG. 3 is a perspective view of the present invention after deliver of the medication, showing the spring locking clip in its most forward or distal position, as carried there by one of the plunger's ratcheted teeth.
Figure 4:
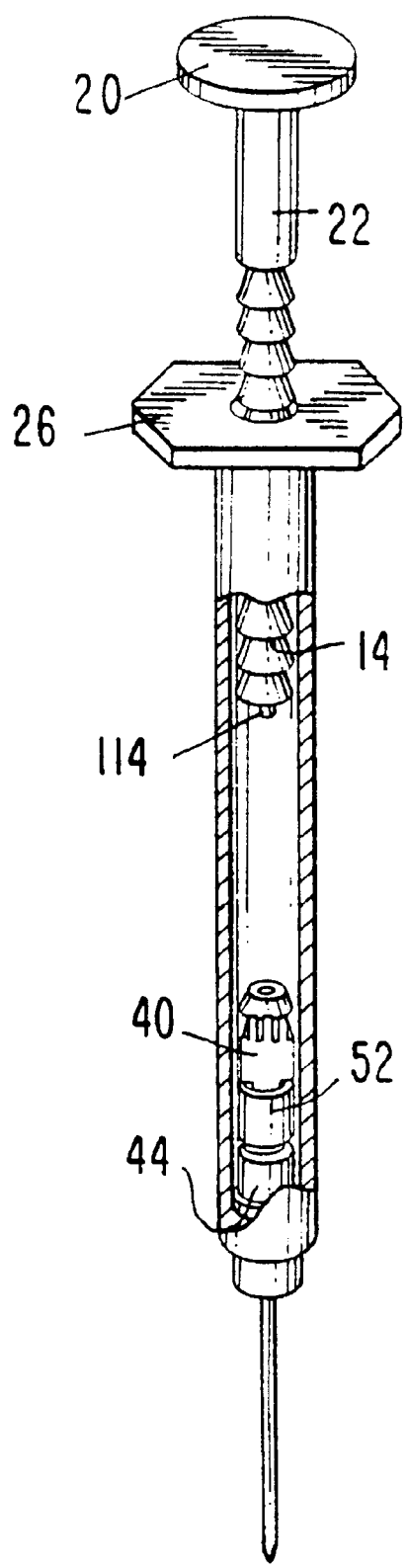
FIG. 4 is a perspective view showing the manner by which the plunger becomes severed, a consequence of a second attempted proximal movement of the plunger.
Figures 5, 5A:
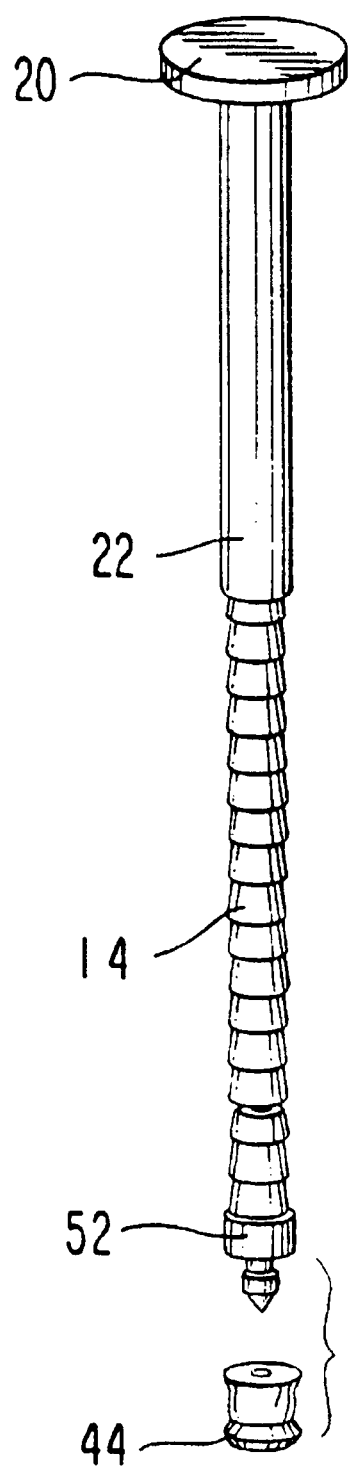
FIG. 5 is a perspective view of an embodiment of the plunger, shown without the piston element.
FIG. 5a is a perspective view of the resilient piston element of the plunger mechanism.

As best seen in the drawings, the present invention, a syringe 10, comprises a main cylinder body 12 and a reciprocating plunger member 14 slidable, received and contained within the cylinder body 12. The preferred material for the cylinder body is a clear medical grade polypropylene which is insoluble and unreactive with most medications and has been FDA approved. The preferred plunger material is medical grade polypropylene modified by the incorporation of a suitable additive so as to provide embrittlement to the resin.

A needle 15 is attached to the distal end of the syringe 10 in a conventional manner. Of course, the syringe can be sold separately from the needle. The details of the construction of the needle and its manner of attachment to the syringe are not believed necessary for a full understanding and appreciation of the present invention. The needle 15 is secured to the tip 18 of the cylinder body 12. For purposes of this description, the end of the cylinder body 12 towards the tip and needle will be referred to as the distal end and direction or motion toward that end is referred to as distal. The other end of the syringe, i.e., the end of the plunger member 14 having the thumbcontacting disc 20 and the finger grips 26 is referred to as the proximal end and direction or motion toward that end is referred to as proximal. As can be seen in the Figures, the thumb-contacting disc 20 is secured to the proximal end of the plunger member 14 and facilitates withdrawal or proximal movement of the plunger member 14 with respect to cylinder body 12 as well as medication dispensing or distal movement of the plunger member 14 toward the tip 18 of the cylinder body 12. The proximal motion aspirates the syringe and then draws medication through the needle and into the barrel or chamber of the syringe while distal motion dispenses medication, held in the barrel, through the tip 18 and the needle 15. The medication is dispensed from the cylinder body or barrel by the sliding action of resilient piston 44 against the inner sidewall 17 of the barrel.

Figure 8:
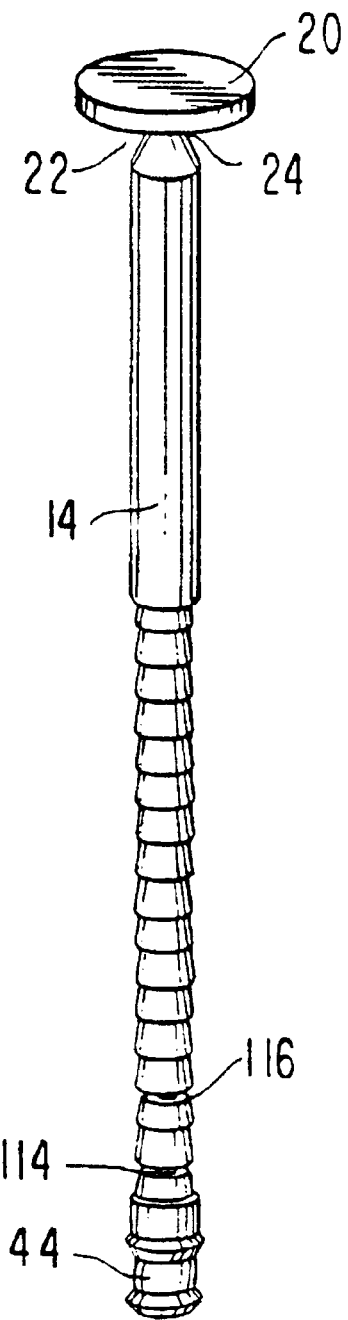
FIG. 8 is a side view of a fourth plunger embodiment containing three reduced areas, one immediately adjacent to the thumb-contacting disc.

The thumb-contacting disc 20 is secured to a segment 22 of the plunger member 14. In the embodiment of the invention shown in FIG. 8, segment 22 is partially frusto-conical and represents a reduced diameter, fracture plane 24. As seen in FIG. 8, the reduced diameter end of segment 22 forms the base for the thumb-contacting disc 20. After use of the syringe, the thumb-contacting disc 20 can be bent with respect to fracture plane 24 until the disc breaks apart or separates. Removal of the thumb-contacting disc 20 disables the syringe, after use, making reuse of the syringe difficult. The removal of disc 20 serves not only to disable the syringe from further reuse, but also as a convenient, compact inventory control mechanism.

Referring back to FIGS. 1–4, the cylinder body 12 is provided, at its proximal end, with a finger grip or finger support plane 26. It provides a convenient finger support surface for the relative reciprocation of the plunger member 14 with respect to cylinder body 12 and provides a rest surface for the user's fingers during use.

The plunger member 14 is a rod, in basic configuration. Frusto-conical ratcheting teeth 28 extend over a portion of the length of the plunger member 14. As can be best seen in the Figures, each ratchet tooth 30 comprises an inclined, outwardly extending (from proximal to distal end) camming or inclined surface 31, and is molded to an adjacent ratchet tooth by a base or common plane 32 having an enlarged diameter D1 (for the upper relative tooth) and a reduced diameter D2 (for the lower relative tooth).

In the embodiment of the invention shown in FIGS. 13–32, the straight, inclined surfaces 31 are replaced by convex surfaces. In this manner, the outside surface of the ratchet teeth are bead-like and provide a smooth surface for the camming of the spring locking clip (during proximal plunger movement) and, yet, movement of the locking clip along with distal movement of the plunger The bead-like ratchet teeth are each provided with a large diameter, about midway between the tooth. It is equivalent to diameter D1 of the frusto-conical ratchet teeth of FIG. 1. The bead-shape of the ratchet teeth provides for smoother operation during plunger withdrawal. Also, the plunger withdrawal force is greatly reduced and found to be nearly the same as when no spring locking clip is used.

Figure 7:
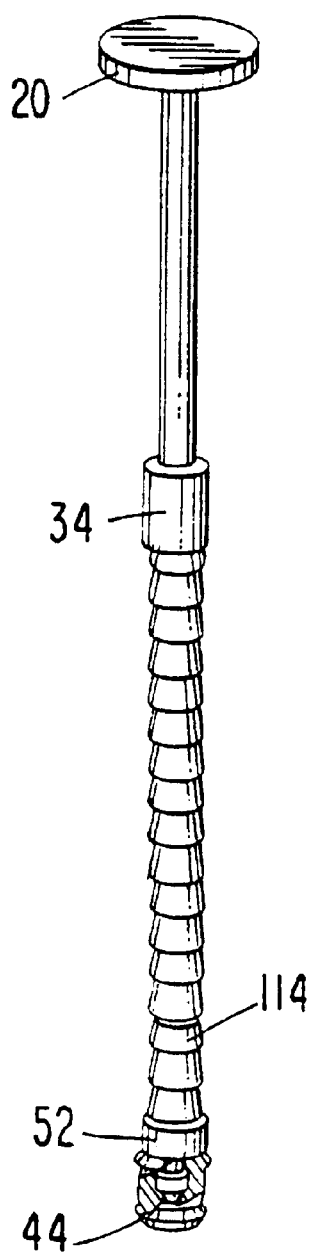
FIG. 7 is a side view of a third plunger embodiment with a single reduced area gap and an enlarged cross-sectional area for preventing tampering.

In the embodiment shown in FIG. 7, a plunger seal 34 encircles plunger member 14 directly above the most proximal ratchet tooth. The plunger seal 34 can be integrally molded or formed with the plunger or, alternatively, it can be a separate resilient component. A close fitting of the plunger seal 34 (or segment 22 of the plunger shown in FIG. 1) to the barrel limits access to the spring locking clip and makes the device tamper proof. The close tolerance of parts between seal 34 (and/or segment 22) and the inner sidewall 17 of the barrel is represented by small gap 41. The plunger seal 34 or segment 22 has an outside diameter larger than the diameter D1 of the ratchet teeth and, in the embodiment of FIG. 7, the plunger seal 34 has a diameter only slightly less than that of the interior sidewall 17 of the barrel. The plunger seal provides a barrier between the outside of the syringe and the ratchet teeth so that foreign objects cannot enter between the plunger seal 34 and the inner sidewall 17 of the cylinder body 12. Thus, the plunger seal 34 or segment 22 serves as a sealing device to prevent unauthorized access to the spring locking clip 40 so that it can not be disabled from its intended use. In an alternate embodiment, the plunger seal 34 is rubber and physically contacts and is, at least in part, partially compressed by the relative diameter of the inner sidewall 17.

The distal end of the plunger member 14 comprises a piston or fluid-pushing sealing member 44. It is preferably made from a rubber-like substance, partially compressible material. Preferably, the piston is a synthetic medically approved rubber. Here, again, the piston 44 may be integrally molded or formed with the plunger or a separate rubber component. As seen in FIGS. 5, 5a and 6–8, the piston can be attached to the distal end of the plunger by a blind hole which is forcibly mounted on a frusto-conical projection, seen in FIG. 7. This secures the rubber piston to the plunger. The piston 44 has a diameter, when radially compressed by the sidewall 17 of the barrel, substantially equal to the diameter of the inner sidewall 17 and provides a sliding, yet sealing, contact therebetween. When the plunger member 14 is reciprocated within the cylinder body 12, all fluid (distal of the piston 44) will be pushed through the tip 18 and, therefore, through the needle 15. The sealing member 44 also prevents any medication or fluid from entering into the cavity above (or proximal) to it. Piston 44, of course, travels along with the plunger member 14 and is physically secured thereto.

Adjacent to the proximal end of piston 44 is an enlarged plunger portion seal section 52 which, similar to plunger seal 34 or segment 22, provides a safety seal to prevent unauthorized access to the ratchet teeth 28 and to the spring locking clip 40. It, too, prevents a paper clip, a knife point, etc. from gaining access into the space proximal of the piston. The diameter of section 52 is about that of the interior sidewall of the cylinder body 12.

Figure 9:
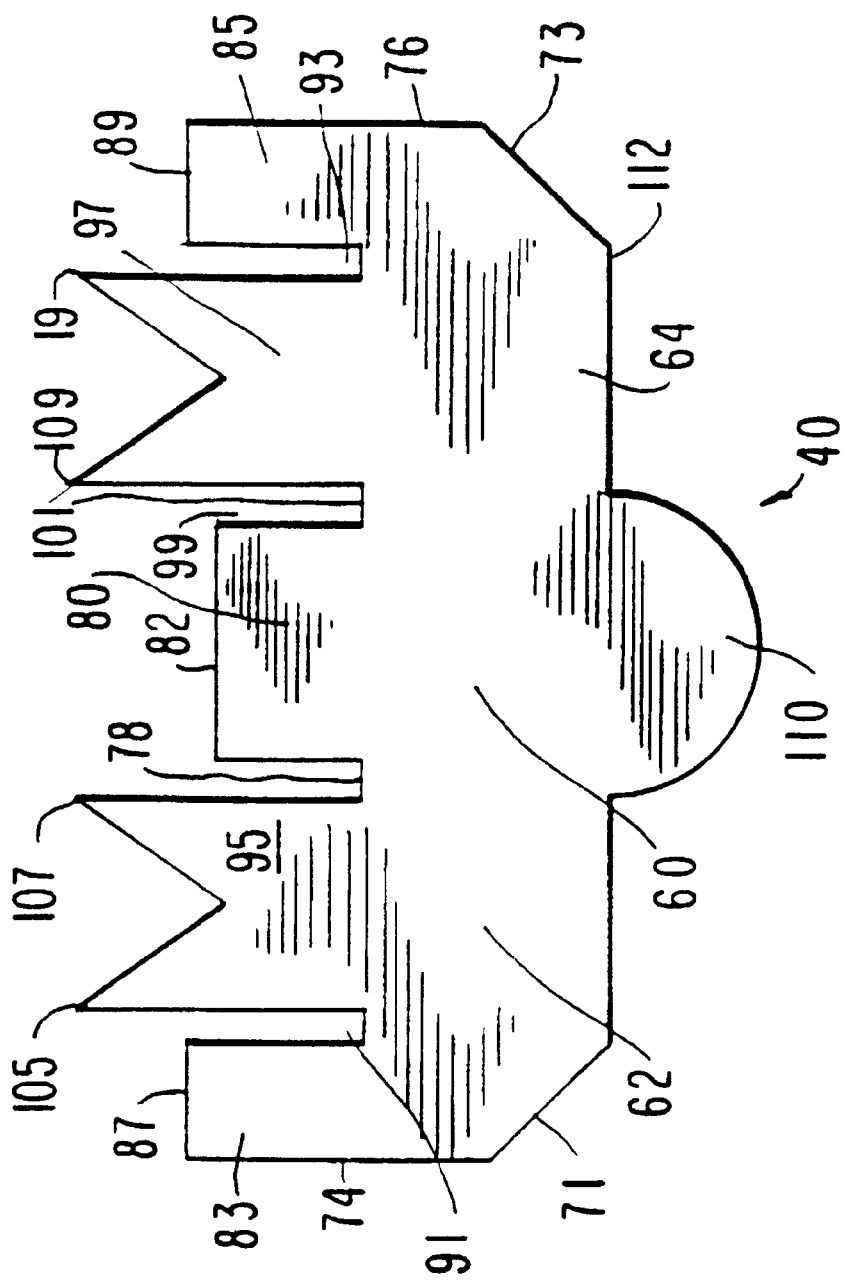
FIG. 9 is a top view of the flat spring locking clip before being formed into its three-dimensional, curved shape for placement and use in the barrel of the syringe.
Figure 10:
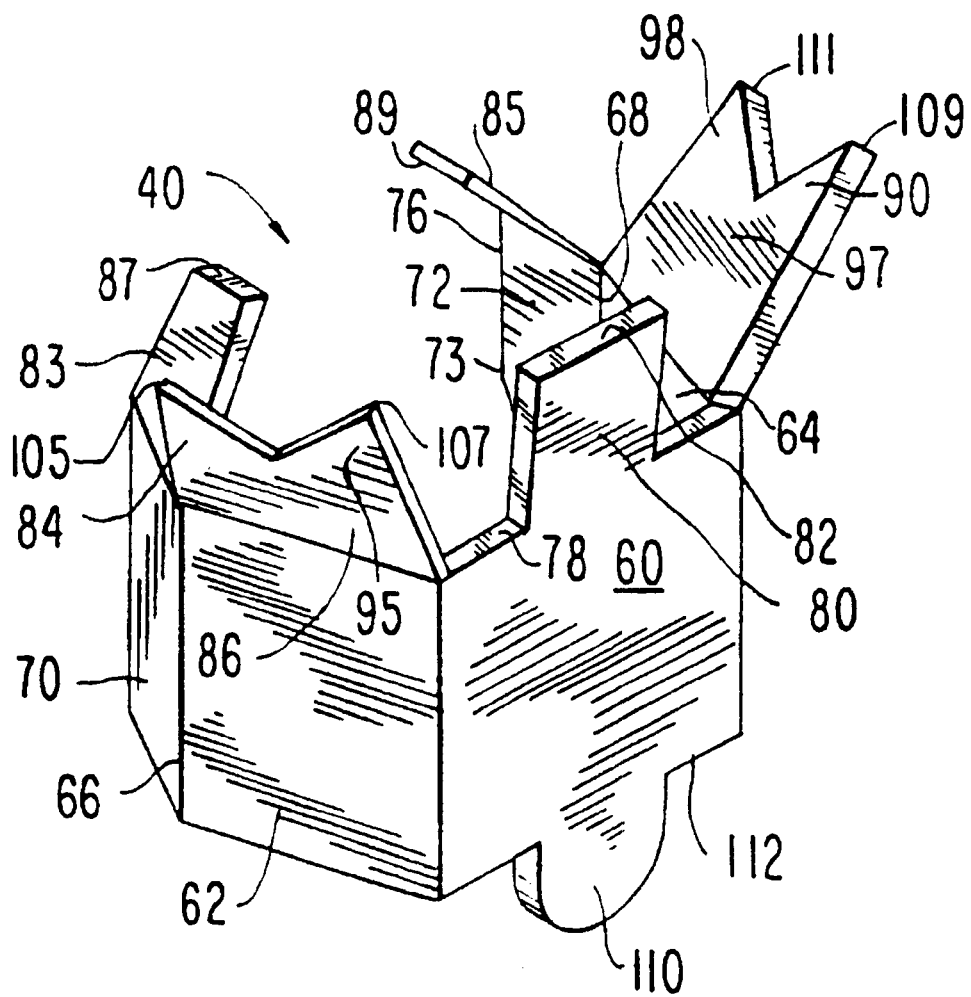
FIG. 10 is a perspective view of the spring locking clip after being formed into shape.
Figure 11:
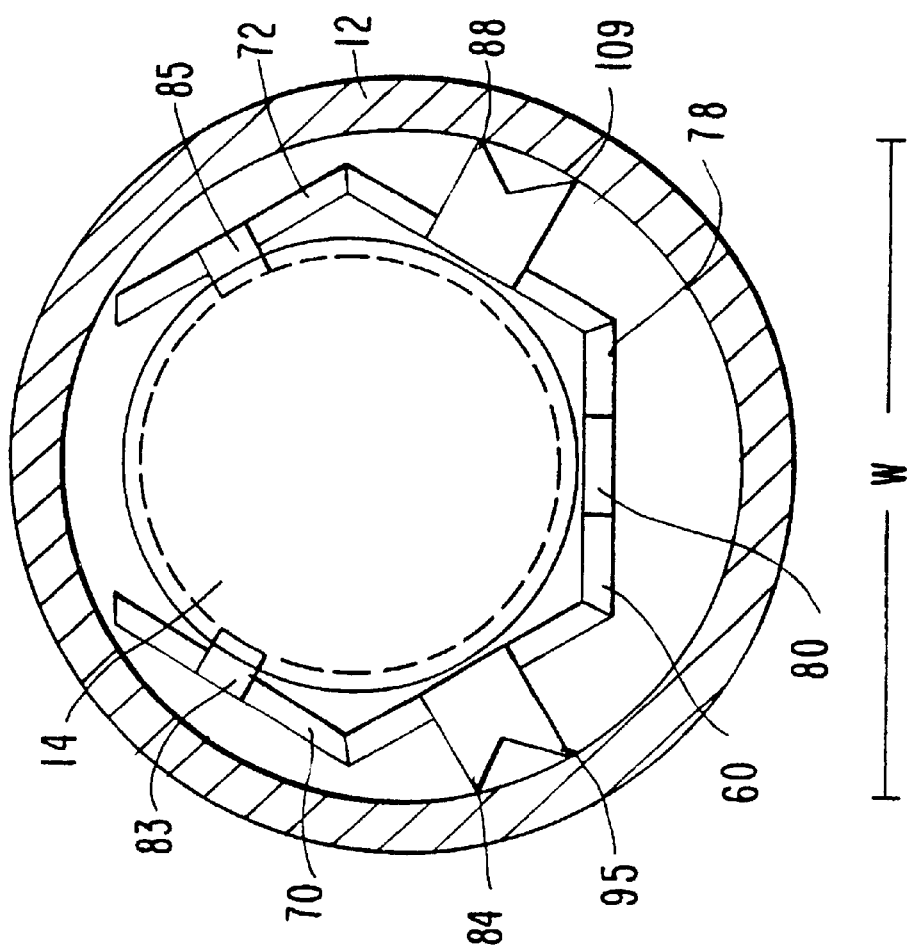
FIG. 11 is a cross section view taken along the lines 11—11 of FIG. 3.
Figure 12:
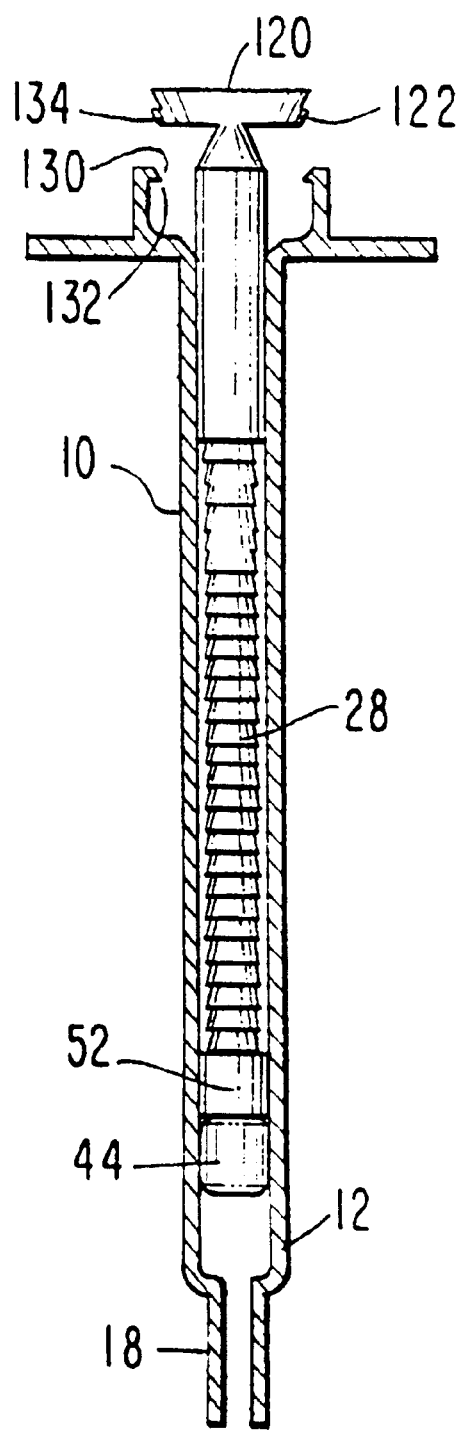
FIG. 12 is a side cross-sectional view of an alternate embodiment of the barrel, plunger and thumb-engaging disc portion of the plunger.

The locking spring 40 is best seen in FIGS. 9, 10 and 11. In the preferred embodiment, when shaped, its basic configuration is that of a hollow six sided figure with one-side open. The overall shape can be semi-cylindrical and extends around the plunger about 200°. Preferably, the spring is formed from a thin piece of resilient metal, preferably a single sheet and thickness of stainless steel. The material must be resilient such that it can be spread apart (by the manufacturer) for initial placement around the particular selected ratchet tooth 30 and, yet, after placement on the plunger member, the locking spring 40 springs back to its original dimensions and configuration. The resiliency also allows the spring locking clip 40 to flex radially inwardly and outwardly, after securement about the plunger member and receipt within the barrel. The locking clip is installed onto the plunger rod by pressing the open end over a ratchet tooth, thereby temporarily spreading its front walls 70 and 72. After initial placement, the spring member can not become dislodged from the plunger, due to the dimension of the open end of the locking clip in comparison to the diameter D1 of the ratchet teeth (whether of the frusto-conical or bead type) of the plunger.

In an alternate version, because of the limited space between the plunger and the inner sidewall 17, occupied by the locking clip 40, the locking clip is secured about the plunger even though it extends less than 180° around the plunger. The dimensioning of the spring locking clip 40 is such that the distance between the edges of front walls 70 and 72 is less than the diameter D1 of the ratchet teeth. It will be appreciated that the locking spring 40 extends about, in one embodiment, at least 180 degrees of the plunger member 14 such that, after placement, it can not accidentally fall off the plunger member. Indeed, in the preferred embodiment it extends about 200°. As an alternate embodiment, when the syringe is constructed to provide 0.1 cc of medication, the locking clip can be circumferentially much smaller. It has been determined that the minimum is about 27° around the plunger.

In a preferred embodiment of the invention, the height h of the spring locking clip 40 is less than the overall width w, when formed. In this manner the locking spring is disc-like and is not elongated. It is thus easier and less expensive to manufacture than an elongated device because it requires less material and can be made with high speed manufacturing apparatus. The drawings illustrate the locking clip as extending over about 2 ratchet teeth (See FIGS. 1 and 2) for ease of illustration only. In actual manufacture, however, the height of the spring locking clip is intended to be less.

The locking clip has a flat back section 60 and a pair of opposed, outwardly extending sidewalls 62 and 64, secured to the side edges of the back section. Extending inwardly from the outermost edges 66 and 68 of sidewalls 62 and 64, respectively, are front walls 70 and 72. Each of back section 60, and sidewalls 62 and 64 are of rectangular configuration. Front walls 70 and 72 have angled edges 71 and 73 respectively (See FIG. 9). The leading vertical edges 74 and 76 of front walls 70 and 72, respectively, are separated by a distance which, as mentioned, is less than the diameter D1 of the base 32 of ratchet teeth 28. In this manner, as mentioned, the spring locking clip 40, during manufacture of the syringe, can expand outwardly over and around a selected ratchet tooth 30 and, yet, as the leading vertical edges 74 and 76 pass over the diameter D1 of a base 32 of a tooth of the plunger, the resiliency of the locking clip forces it to reassume its original dimensions. In this manner, the spring will not accidentally fall off or be removed from the plunger member unless physical force is deliberately applied thereto. As mentioned, in the alternate embodiment of the invention where the locking clip is less than 180°, even extending down to about 27° for syringes of 1 cc size capable of delivering dosages as low as 0.1 cc, the locking clip can not be removed from the plunger after insertion into the barrel since the interior space of the barrel is to a large degree consumed by the plunger and the clip. The clip then has no ability to move away from the plunger. Rather it is sandwiched between inner sidewall 17 of the barrel and the plunger.

A top edge 78 extends along back section 60. Extending upwardly from top edge 78, basically centered along back section 60, is a tab 80. Tab 80 has an edge 82 configured to be able to touch the outside edge of the base 32 of a ratchet tooth. Tab 80 is coplanar with back section 60. The tab, touching the edge of the plunger teeth, prevents rocking motion of the clip on the plunger during plunger movement and ensures alignment between clip and plunger. The tab prevents jamming and facilitates stabilization.

Proximally and inwardly directed camming teeth 83 and 85 extend upwardly from front walls 70 and 73 respectively. The locking clip 40 when placed on the plunger dangles on the selected ratchet tooth (again, whether of frusto-conical or bead-like shape). The inwardly angled camming teeth force the clip to be moved distally during a delivery stroke. More specifically, they come into contact with the base 32 of the ratchet tooth to which the clip dangles upon. The clip is pushed distally as the plunger is moved distally. Gaps 91 and 93 (see FIG. 9) are flexibility control gaps which modify the flexibility of the camming teeth. Top edges 87 and 89 will initially rest on inclined surface 31 of the ratchet tooth or on the smooth bead-like walls in the embodiment wherein the teeth are bead-like. The top edges 87 and 89 will, upon distal movement of the plunger, abut beneath the base of a ratchet tooth so that distal movement of the plunger carries the clip along with the plunger. Yet, the resiliency of the teeth 83 and 85 allows, via radial flexing of the clip, the teeth to cam over and ride on the inclined surfaces 31 or convex surfaces of the ratchet teeth of the plunger, as the plunger is moved proximally, when the spring locking clip is held in its position, inside the barrel, by the action of the locking teeth 84, 86, 88 and 90 embedding into the inner sidewall 17 of the barrel.

Movement of plunger 14 in the distal direction forces the locking spring to move with it since a base 32 of a ratchet tooth pushes on top edges 87 and 89 of camming teeth 83 and 85. However, the resiliency of locking clip 40 allows for the plunger to move proximally with respect to the held-in-position or stationary locking clip 40 since the camming teeth will cam or ride over inclined or convex surfaces 31.

Extending proximally and outwardly from the top edge of sidewalls 62 and 64 are locking teeth 84, 86, 88 and 90. Locking teeth 84 and 86 extend from sidewall 62 and locking teeth 88 and 90 extend from sidewall 64. The localized sections 95 and 97 carry the locking and embedding teeth 84 86, 88 and 90 and serve to reinforce their action. Flexibility control gaps 99 and 101 provide control to the flexibility of sections 95 and 97. The locking teeth are of triangular configuration and terminate in contact points 105, 107, 109 and 111. The contact points extend outwardly from the outside planar surface of sidewalls 62 and 64 and, indeed, the locking points contact the interior sidewall 17 of the cylinder body 12. They bear against the sidewall. The hardness of the contact points is greater than the hardness of the interior sidewall 17 of the cylinder body 12 such that the contact points will dig and embed into the interior sidewall surface of the cylinder body when the locking spring 40 is attempted to be moved by the plunger in the proximal direction. The radial outward resiliency of the spring locking clip embeds the contact points into sidewall 17. When such proximal movement is attempted, the contact points prevent the locking clip from moving proximally. The locking clip can, however, move distally since the contact points radially flex inwardly and will slide over the interior sidewall 17 during plunger movement in the distal direction. The shape and resiliency of the device allows for the discussed radial flexing movement. The distance between contact points 105 or 107, and 109 or 111. may be less than the interior sidewall diameter of the cylinder body 12, and, yet, since the contact points extend outwardly with respect to the outside planar surface of the sidewalls 62 and 64, all contact points 105, 107, 109 and 111 are expected to contact the interior sidewall 17 of the cylinder body 12. The use of multiple contact points ensures embedding of the locking clip, even if there are tolerance irregularities to the inner sidewall 17 of the barrel.

A semicircular tab 110 extends distally from back 60. It counterbalances tab 80 and further prevents jamming of the clip during plunger movement. It extends i.e., is bent radially inwardly towards the plunger, at or about edge 112. Tab 110 provides for smooth distal movement of the plunger and clip without scraping the inside of the barrel. When the plunger is fully moved in the distal direction, tab 110 is actually forced between the plunger seal 52 and the sidewall 17 further locking the clip in the distal location.

The construction, manufacture and use of the device is as follows: The cylinder body 12 is formed in the same manner and with the same materials as is currently done in connection with conventional medical syringes. The plunger member 14, with its ratchet teeth (whether bead-like or frusto-conical) and seals 34 and 52, is preferably formed as a single plastic molded product. In the preferred embodiment the plunger is formed from a plastic having an embrittlement additive. The rubber piston 44 is attached to the plunger. The manufacturer determines the maximum dosage for a particular batch of syringes. The manufacturer has a choice, either to down size the syringe barrel for a particular maximum dosage and/or adjust the location of the spring locking clip on the plunger rod to be used, in a more standard size syringe. With that maximum dosage in mind, the locking spring 40 will be placed on the ratchet tooth 30 which corresponds to the maximum desired dosage. The individual ratchet teeth can be marked or imprinted during molding with suitable identifying indicia to facilitate the location of the locking clip 40 about the particular ratchet tooth which corresponds to a particular maximum dosage.

Placement of the spring clip is accomplished by spreading front walls 70 and 72, camming vertical edges 74 and 76 over base 32. Locating the locking clip 40 toward the distal end of the plunger member 14 provides a smaller maximum dosage for the syringe than locating the same locking clip 40 toward the proximal end. During placement of the clip, the edges 74 and 76 of the clip physically spread such that the distance between them becomes equal to the diameter D1 of the base 32 of a ratchet tooth. This is accomplished by the radial resiliency of the spring clip. The clip can be slid onto the plunger. The clip is not firmly held against the plunger, but, rather, the camming teeth 83 and 85 touch the inclined or convex surface 31 so that the locking clip dangles from a ratchet tooth.

When the leading edges pass the diameter D1 of the ratchet plunger member, the resiliency of the spring locking clip forces the edges 74 and 76 to once again assume their original dimension. In this manner, it should be appreciated by those of ordinary skill in the art that the locking clip 40 is located around the plunger member such that the clip cannot be easily removed without applying physical force to once again spread apart edges 74 and 76. The locking clip is held on the plunger by the greater than 180° configuration and by the camming teeth 83 and 85 resting on the inclined surface 31 of the ratchet tooth. The locking clip does not grip a ratchet tooth but is loosely held onto the tooth's inclined or convex surface. Top edges 87 and 89 of teeth 83 and 85 are, as mentioned, projected or bent inwardly a sufficient distance such that they bear against and touch the incline or convex surface 31 of a particular ratchet tooth.

Locking clip 40 can not move proximally with respect to the plunger member 14 since that relative movement is blocked by the mechanical interaction of top edges 87 and 89 of the camming teeth beneath the base of the upwardly adjacent ratchet tooth. With the locking clip located at the desired position, the manufacturer completes the assembly process by securing the plunger member 14 along with the locking clip 40 into the cylinder body or barrel. The resiliency of the spring allows for the plunger and clip to be inserted into the barrel. The article is then packaged and delivered to the end user.

Figure 15:
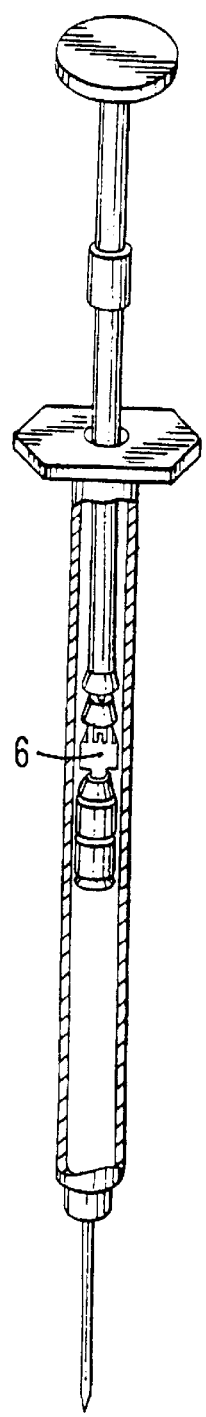
FIG. 15 is a plan elevational view, similar to FIGS. 13 and 14 with the plunger fully withdrawn, i.e., the spring locking clip has been cammed over the surface of the bead-like ratchet teeth until the spring locking clip's projecting barbs are forced into the inside wall of the barrel. This prevents the locking clip and the plunger from being further withdrawn; the medicine is fully drawn into the barrel during this stage and the device is ready for dispensing medication.
Figure 16:
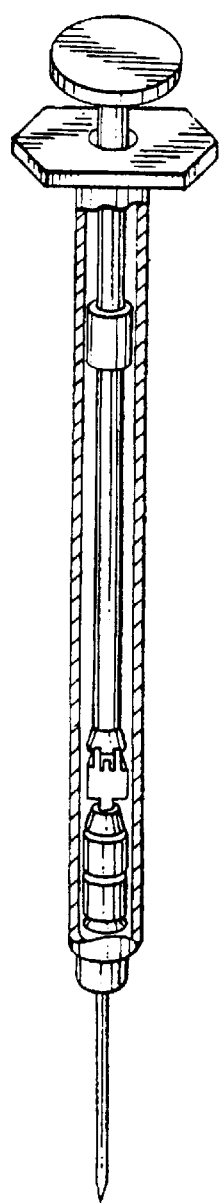
FIG. 16 is a plan elevational view, similar to FIGS. 13–15 with the plunger shown in its fully, projected position, i.e., fully distal after medicine dispensing. The locking, spring clip has moved distally, along with the plunger by cooperation with the base of a ratchet tooth. Further plunger withdrawal is blocked by the embedding of the spring clip's barbs into the sidewall of the barrel.

In the embodiment of the invention shown in FIGS. 13–33, the syringe plunger is provided with an aspirating gap 114 between either the disc-like thumb element and a ratchet tooth or between two frusto-conical or bead-like ratchet teeth. The length of the aspirating gap will be determined by the manufacturer. The aspirating gap 114 allows the plunger to be reciprocated, i.e., moved proximally and rearwardly, for aspirating, without moving the locking clip during the distal plunger movement. No movement of the locking clip will occur so long as the clip is located on the aspirating gap, even though the plunger is moved proximally and distally one or more times. The locking clip will only serve its "single-use" function when the plunger is proximally withdrawn to such an extent that the locking clip cams over at least the immediately distal ratchet tooth. Then, as seen in FIGS. 15 and 16, distal movement of the plunger moves the locking clip.

In the embodiment shown in FIGS. 1–12, the needle 15 is inserted into the vial of medication and the thumb-contacting disc 20 moved proximally with respect to finger grip 26. During plunger retraction or proximal movement, locking clip 40 will remain fixed in the barrel, a consequence of outward radial flexing of the locking spring thereby embedding the teeth into the sidewalls. The plunger can move proximally until the top edge of seal 52 contacts the bottom edge 112 of the locking clip 40. Once this abutment occurs, further proximal movement of the plunger member 14 can not happen since the contact points 105, 107, 109 and 111 of the locking teeth 84, 86, 88 and 90 are physically digging into the interior sidewall 17 of the cylinder body 12.

It should be appreciated by those of ordinary skill in the art that the locking clip 40 cannot move when the plunger member 14 is proximally moved. The contact points prevent any proximal movement of the locking clip. Initial location of the locking clip and thus locking teeth 84, 86, 88 and 90 with respect to the plunger determines the maximum amount of relative reciprocation of the plunger in the barrel and thus the maximum dosage which can be administered by the syringe. During proximal plunger movement, the tab 80 and tab 110 of the locking clip glide or cam over the edges of the ratchet teeth. Together they maintain alignment and prevent jamming of the device. As plunger member 14 is withdrawn or moved proximally with respect to cylinder body 12, the radial resiliency of the teeth of spring locking clip 40 is such that the edges 87 and 89 will travel over each inclined or bead-like surface 31 of each ratchet tooth 30. Since the locking clip is maintained within the cylinder body 12 in relative position by the interaction of the contact points 105, 107, 109 and 111 against the inside cylindrical surface 17 of the cylinder body 12, the plunger member 14 can be fully withdrawn until seal section 52 contacts the bottom edge 112 of the locking clip 40. When this occurs, however, further proximal movement of the plunger member 14 is mechanically blocked since further desired proximal movement of the plunger will only further embed the contact points into the inner sidewall 17 of the cylinder body 12. Thus, the plunger member is restricted in its relative movement with respect to the cylinder body.

With the medication now contained within the cylinder body 12, more specifically, between piston 44 (or 109 of FIG. 13) and the tip 18 of cylinder body 12, the user is ready to dispense the medication through needle 15, as and when desired. The needle is inserted through the patient's skin and the user then applies pressure onto thumb-contacting disc 20 such that plunger member 14 is moved distally, thereby pushing piston 44 distally and, thereby, dispensing all medication through tip 18 and needle 15. Since top edges 87 and 89 of camming teeth 83 and 85 will be pushed distally by contact with the base 32 of the above-located ratchet tooth, the locking clip 40 will flex radially inwardly and slide distally within the barrel, as plunger member 14 is distally moved to dispense medication. The contact points only prevent proximal movement of the locking spring; distal movement is allowed by the sliding of the contact points along the interior sidewall and the inherent resiliency of the locking clip.

After all medication has been dispensed from the syringe, the seal 52, above piston 44, abuts against the bottom edge 112 of the locking clip. This is shown with the aspirating embodiment in FIG. 16. A second reciprocation of the plunger member 14 with respect to cylinder body 12 is mechanically blocked since locking clip 40 (106 in FIGS. 13–16) adjacent to the seal 52 will embed into the sidewall 17 as the plunger is attempted to be moved proximally a second time. It is prevented from a second proximal movement by contact points 105, 107, 109 and 111 digging into the interior sidewall 17 of the cylinder body 12. Thus, it should be apparent, that a second reciprocation, to draw medication or drugs into the syringe 10, is mechanically blocked since the plunger member 14 cannot move a second time in the proximal direction with respect to cylinder body 12.

To further disable the syringe 10 for subsequent potential use, the user can, if desired, bend or twist the thumbcontacting disc 20 along the fracture plane 24, until it breaks apart. Without the thumb-contacting disc 20 secured to the plunger member 14, it is far more difficult to reciprocate the plunger member 14, in either direction, even assuming that one could first disable the spring locking clip mechanism. Furthermore, the thumb-contacting disc 20 can now serve as a means to limit syringe distribution. For example, a certain number of such discs may be collected and turned into the manufacturer or dispenser in exchange for a like number of new syringes. Inventory and audit control are easier to keep track of with the flat discs than with the bulky syringes.

In an alternate embodiment of the present invention, the thumb-contacting disc is provided (see FIG. 12) with an inclined thumb section 120, and a second, inclined outer wall disc-like section 122. Together these comprise an annular male dove-like arrangement for the plunger. The proximal portion of the cylinder body 12, adjacent the finger grip 26, .is provided with an annular inwardly directed edge 130, terminating in a locking lip 132. Together these comprise an annular female, dove-tail like arrangement for the barrel. Thus, when the thumb-contacting disc 20 is fully reciprocated in the distal direction, inclined outer wall 122 slides until the locking lip 132 will overlap the second annular disc-like section 122, thereby preventing any further proximal or distal movement of the plunger with respect to the cylinder body 12. Thus, it should be appreciated and apparent to those of ordinary skill in the art that the smallest diameter of the edge 130, at the point of locking lip 132, is less than the largest diameter of edge surface 134, although the resiliency of the barrel and a split at the proximal end allows edge 130 to cam over edge 134 until held by locking lip 132.

Figure 6:
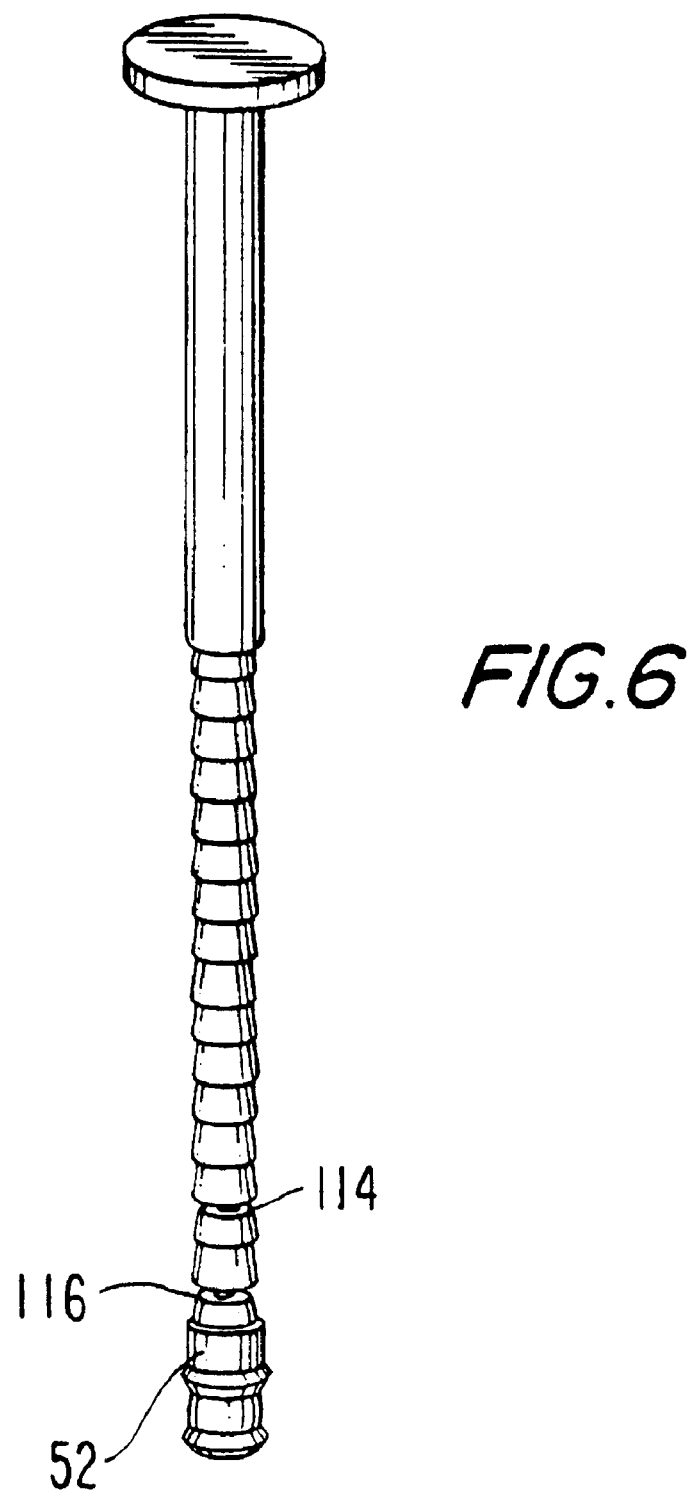
FIG. 6 is a side plan view of a second embodiment of a plunger, this version containing two reduced area gaps between ratchet teeth.

In yet another alternate embodiment of the invention, a mechanism is provided to thwart tampering with the locking mechanism. After the first full distal movement of the plunger, the locking clip is embedded into the sidewall of the syringe, adjacent to seal 52. The distal force needed to overcome the force of the locking clip being embedded into the sidewall of the barrel exceeds the tensile strength of the plunger such that a second attempted proximal movement will result in a physical separation of the plunger along its length, preferably just above the locking clip (see FIGS. 4 and 17). To localize severing at that location, a reduced diameter section of the plunger is located above the seal section 52. In the preferred embodiment the reduced cross-sectional area of the plunger is located so that the break will occur just above the proximal surface of the clip. As seen in FIGS. 6, 7 and 8, two or more reduced areas 114 and 116 are provided as potential areas to be severed by the movement of the plunger.

As best seen in FIG. 11 the radial resiliency and strength of the locking clip actually moves and forces the plunger out of axial alignment with the axis of the barrel. Thus, in very small diameter and volume syringes, a locking clip can be provided which still functions to block reuse. Only a single thickness of metal across all diameters of the barrel is required between the plunger and the sidewall of the barrel. In an alternate embodiment, because the clip is not acting symmetrically around the plunger but, rather, asymmetrically, the locking clip can be made as small as to extend about 27° of the 360° plunger. In this manner, very small capacity syringes with a locking non-reusable mechanism can be achieved. The vector forces of the locking teeth push the plunger out of alignment.

Figure 13:
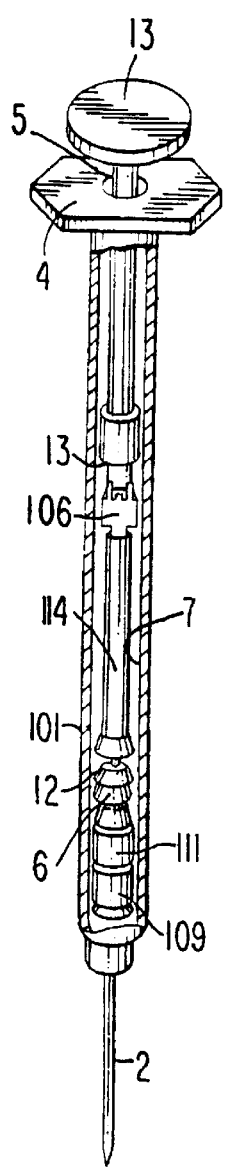
FIG. 13 is a plan elevation of the preferred embodiment of the present invention, having bead-like ratchet teeth on the plunger rod and an aspirating gap between ratchet teeth, the single use syringe is shown in its initial stage, i.e., prior to aspirating and prior to the intake of the medicine to be dispensed.
Figure 14:
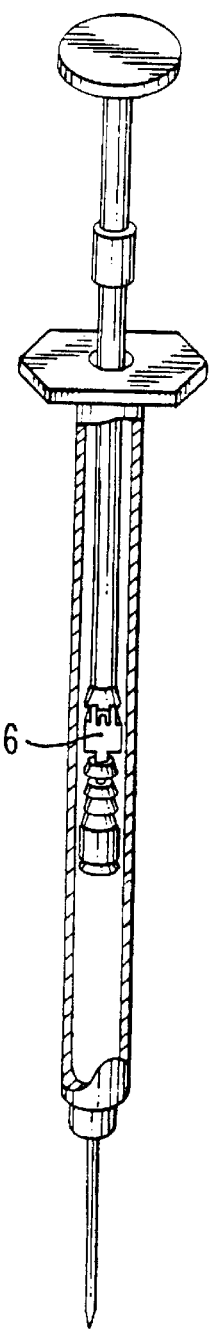
FIG. 14 is a plan elevational view, similar to FIG. 13, with the plunger partially withdrawn, i.e., moved in the proximal direction, for first aspirating and then drawing in medication.
Figure 18:
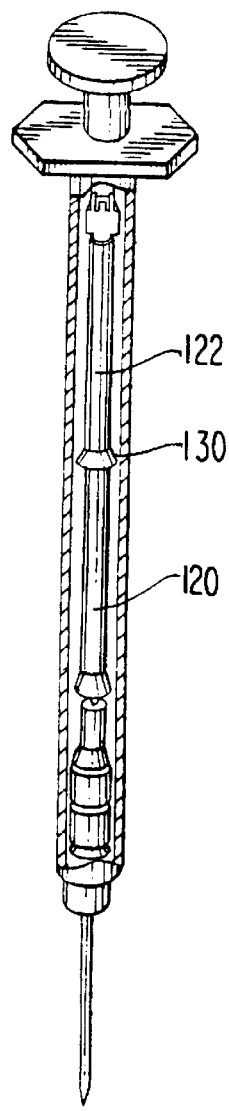
FIG. 18 is a plan elevational view, similar to FIG. 13 showing another embodiment of the present invention wherein the plunger has bead-like ratchet teeth and two aspirating gaps are located between ratchet teeth, for providing aspiration between two medicine injecting strokes of the syringe, i.e., two partial doses can be supplied by the syringe with each dose being preceded by an aspirating cycle. The syringe is shown in its initial stage, i.e., prior to even a first aspirating cycle and prior to the plunger being even partially withdrawn.

FIG. 18 is a plan elevational view, similar to FIG. 13 showing another embodiment of the present invention. The frusto-conical ratchet teeth have been replaced with the bead-like ratchet teeth. Two aspirating gaps 120 and 122 are provided to the plunger, with a single ratchet tooth therebetween. The gap is defined on its distal end by a ratchet tooth. The diameter of the rod at the gap is less than the inside diameter of the clip so that they can easily reciprocate without movement of the clip. The two aspirating gaps allow for aspiration before each of two medicine intake strokes of the syringe, i.e., two partial doses can be supplied by the syringe with each dose being preceded by an aspirating cycle. The syringe is shown in FIG. 18 in its initial stage, i.e., prior to even a first aspirating cycle and prior to the plunger being even partially withdrawn.

Figure 19:
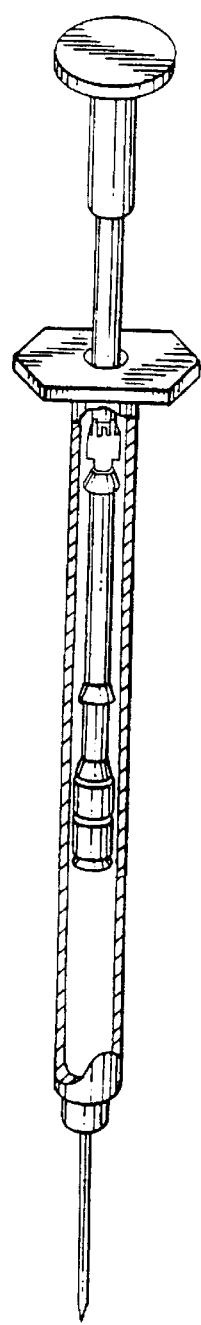
FIG. 19 is a plan elevational view, similar to FIG. 18 with the plunger partially withdrawn for aspirating the barrel, prior to filling the barrel with medicine for dispensing.
Figure 20:
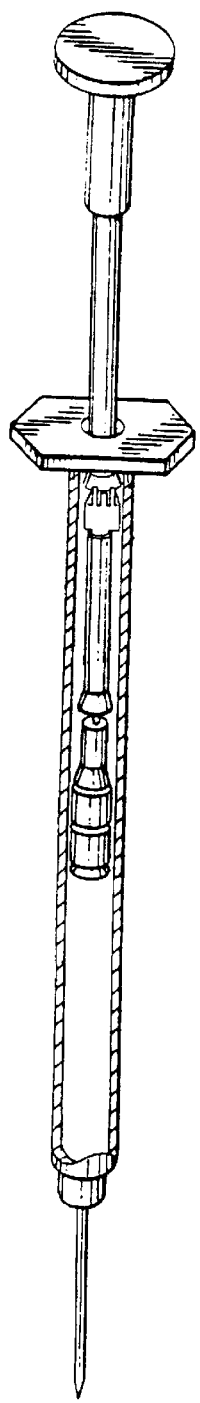
FIG. 20 is a plan elevational view, similar to FIGS. 18 and 19, with the plunger withdrawn such that the spring locking clip has cammed over the surface of the first, bead-like ratchet tooth. In this position, the medicine has been withdrawn into the barrel. The first dose of medication is ready to be dispensed.
Figure 21:
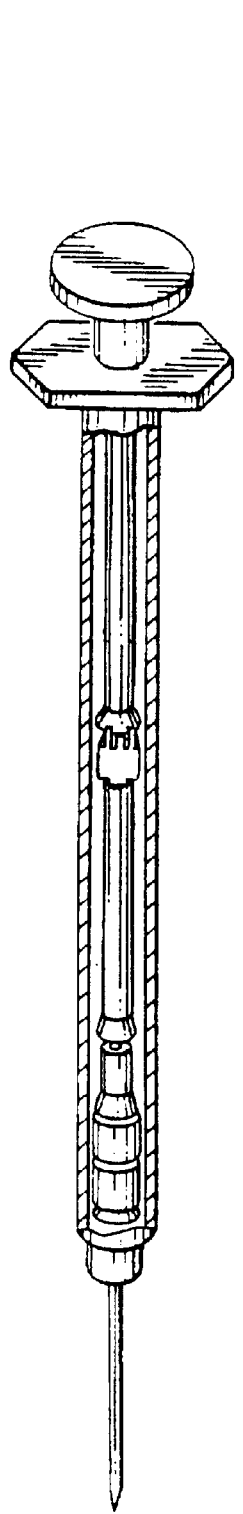
FIG. 21 is a plan elevational view, similar to FIGS. 18–20, with the plunger pushed distally, fully, a first time to dispense all medication drawn into the barrel. The locking, spring clip is shown as having moved to a point midway along the plunger rod since it moved there as the plunger moved. The syringe is ready for a second aspiration and medication dispensing.

FIG. 19 is a plan elevational view, similar to FIG. 18, with the plunger partially withdrawn first for aspirating and then withdrawn for filling the barrel with medicine for dispensing. The plunger rod can be reciprocated until the user makes the conscious effort to withdraw the plunger rod to such an extent that the locking clip cams over the first ratchet teeth tooth 130. During that proximal stroke, medication must be drawn into the barrel. So long as the locking clip is between ratchet teeth, i.e., on the aspirating gap, the plunger can be moved proximally and distally one or more times. Once the plunger rod is pulled proximally so that the locking clip cams over the ratchet tooth 130, a distal motion of the plunger rod dispenses medication and move the locking clip distally. FIG. 20 is a plan elevational view, similar to FIG. 18 with the plunger withdrawn such that the first ratchet tooth distal to the aspirating gap 122 has been cammed over by the locking clip. In this position, the medicine has been drawn into the barrel. FIG. 21 is a plan elevational view, similar to FIG. 18 with the plunger pushed distally, fully, a first time to dispense all medication drawn into the barrel. The spring locking clip is shown as having moved toward the distal end of the syringe since it moves in that direction as the plunger moves. As can be seen, the spring locking clip has moved to a midway position between the distal and proximal ends of the syringe.

Figure 22:
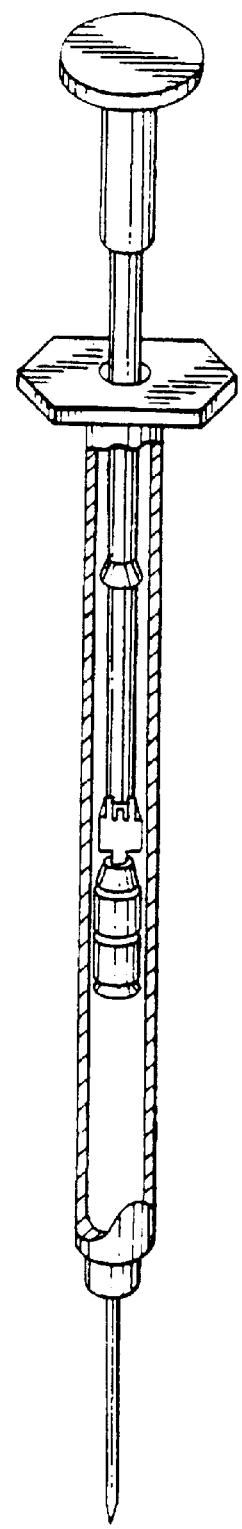
FIG. 22 is a plan elevational view, similar to FIG. 19, showing the plunger rod being withdrawn, a second time, for aspirating and loading of the barrel with a second dose of medicine. Further removal of the plunger cams the spring locking clip over the ratchet tooth.

FIG. 22 is a plan elevational view, similar to FIG. 18, showing the plunger rod being withdrawn a second time for aspirating prior to loading of the barrel with medicine.

Figures 23, 24, 25:
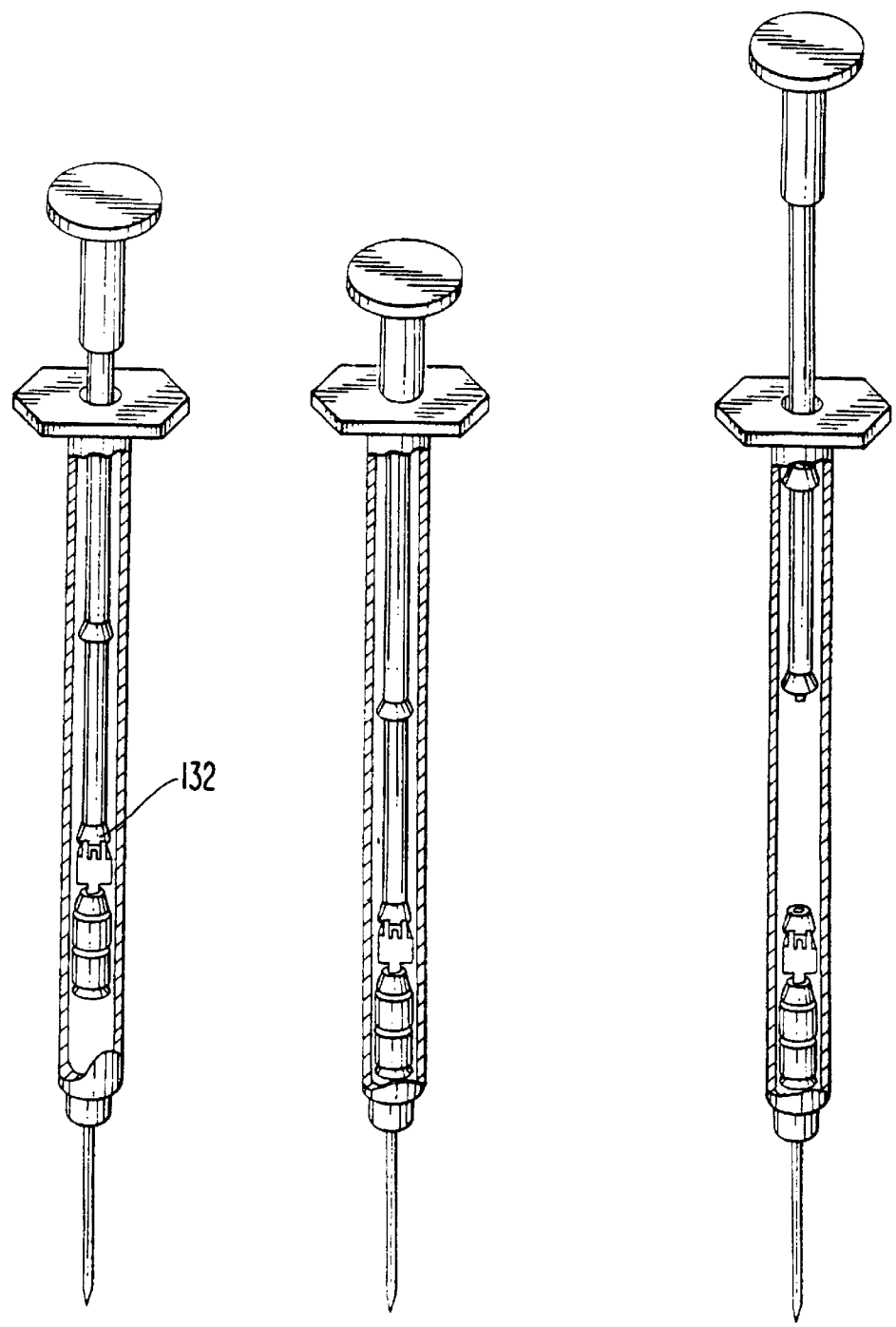
FIG. 23 is a plan elevational view, similar to FIGS. 18–22, showing the plunger rod moved to the distal position, to dispense medication. The spring locking clip is shown as having moved with the plunger rod.
FIG. 24 is a plan elevational view, similar to FIGS. 18–23, showing the plunger rod moved fully into its distal position, dispensing all medicine and moving the spring locking clip to its full, distal position.
FIG. 25 is a plan elevational view, similar to FIGS. 18–24, showing the plunger rod broken apart as a consequence of an attempted additional withdrawal of the plunger. The force of attempted withdrawal has exceeded the structural strength of the plunger rod, thereby resulting in the break at the fracture plane. The embedding force of the spring locking clip exceeds the tensile strength of the plunger rod.

Again, the plunger rod can move proximally and distally, without movement of the spring locking clip, to the extent that the clip is on the aspirating gap 120, and not in contact with the base of a ratchet tooth. FIG. 23 is a plan elevational view, similar to FIG. 18, showing the plunger rod in a position as it moves in the distal direction to dispense medication. The spring locking clip is shown as having moved with the plunger rod. This is because the clip has come into contact with the ratchet tooth 132, more specifically, the ratchet tooth engaging portion of the clip is below the base of the ratchet tooth 132 and distal movement of the rod moves the clip. FIG. 24 is a plan elevational view, similar to FIG. 21, showing the plunger rod moved fully into its distal position, dispensing all medicine and moving the spring locking clip to its full, distal position. A further retraction of the plunger is prevented by the spring locking clip's barbs embedding into the inside barrel wall of the syringe.

Figure 17:
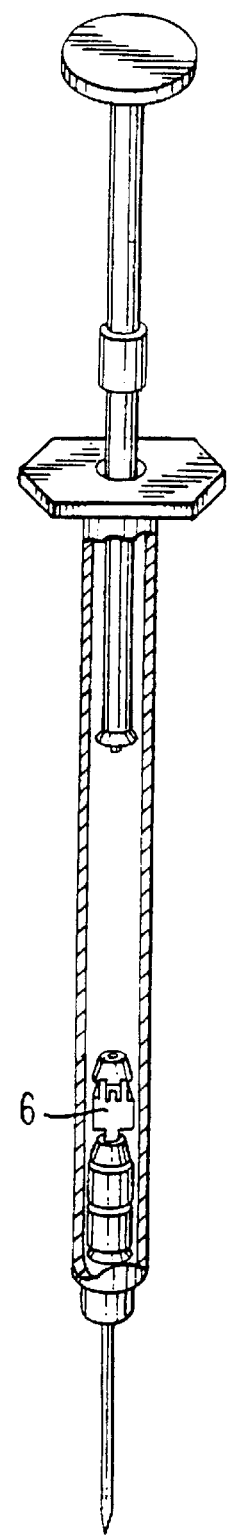
FIG. 17 is a plan elevational view, similar to FIGS. 13–16, after a second attempted retraction of the plunger is tried, i.e., after the plunger has been fully moved distally to first dispense a full load of medication. The plunger is shown broken apart by the force of withdrawal of the plunger being greater than the tensile strength of the plunger. The force of withdrawal cannot overcome the force of the spring locking clip embedding into the barrel side wall and the plunger rod breaks at the fracture plane.

FIG. 25 is a plan elevational view, similar to FIG. 17, showing the plunger rod broken apart as a consequence of an attempted additional withdrawal of the plunger. The force of attempted withdrawal has exceeded the structural strength of the plunger rod, thereby resulting in the break. The embedding force of the spring clip exceeds the force of withdrawal. The break has occurred at a fracture plane.

Figure 26:
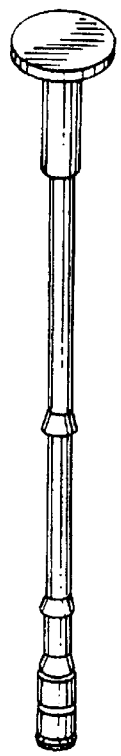
FIGS. 26–33 show alternate embodiments of the plunger rod varying the number and location of the ratchet teeth and the number, location and length of the aspirating gaps.
Figure 27:
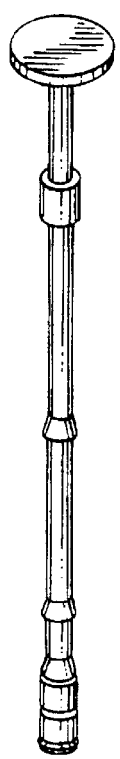
Figure 28:
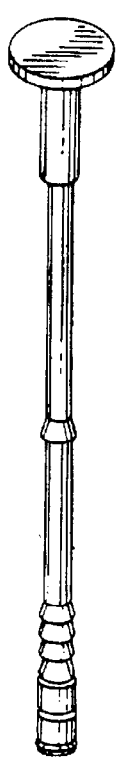
Figure 29:
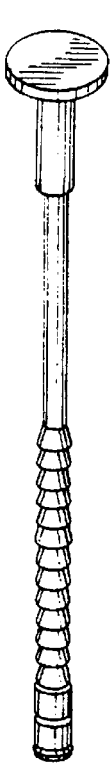
Figure 30:
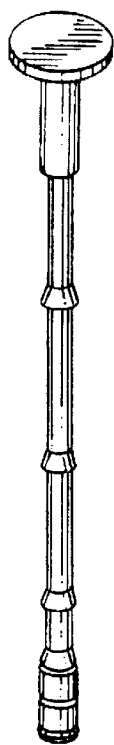
Figure 31:
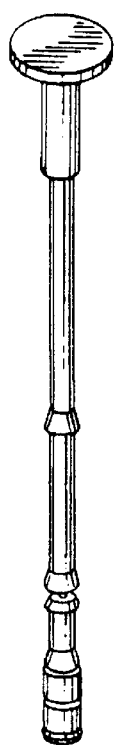
Figure 32:
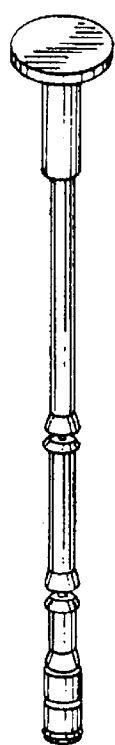
Figure 33:
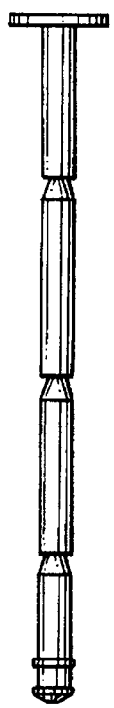

FIG. 26 shows the plunger element, provided with two large aspirating gaps and one small aspirating gap, the medication pushing piston, and the sealing piston, prior to positioning of the spring locking clip on the rod and prior to placement within the syringe barrel. FIG. 27 shows a plunger having a sliding tube at the proximal end for easing the axial sliding of the plunger within the barrel of the syringe. The sliding tube also blocks access into the barrel by a foreign object. As can be seen, the underside of the thumb engaging pushing disc is modified. FIG. 28 shows a plunger with two aspirating gaps. FIG. 29 shows the plunger, with bead-like ratchet teeth with a single aspirating gap. This plunger can be used by the manufacturer for a large range of volumes of the same barrel, dependent upon where the user commences medication dispensing, i.e., the location of the clip along the ratchet teeth. FIG. 30 shows an embodiment of the plunger with three large aspirating gaps and one small aspirating gap. This plunger could be used to dispense four doses of medication, with each dose received by the syringe barrel preceded by an aspiration movement. FIG. 31 shows the plunger of FIG. 26 as it breaks at a fracture plane when a user, after a single use medication dispensing operation has occurred (in two doses) tries to reuse the syringe a second time and the force of withdrawal exceeds the structural strength of the plunger. In this case, however, the embedding force of the spring clip into the sidewall of the barrel exceeds the strength of the plunger rod. FIG. 32 also illustrates the fracture planes or breakage points of the plunger shown in FIG. 26. The plunger can be provided with one or more breakage points to further ensure that repeated use of the syringe cannot occur. The plunger will break at either break point if a user, after full use has first occurred, tries to withdraw the plunger and the force of attempted withdrawal exceeds the structural strength of the plunger. FIG. 33 is another embodiment showing the plunger rod provided with three ratchet teeth.

There have been described several embodiments of a single-use hypodermic needle and syringe assembly. While the invention has been described with reference to specific embodiments, the description is illustrative of the invention and is not to be construed as limiting the invention. Various modifications and applications may occur to those skilled in the art without departing from the true spirit and scope of the invention.

We claim:
1. A single-use and aspirating-capable syringe comprising:
   a hollow barrel having an interior cylindrical sidewall, a distal end and a proximal end opposite to said distal end,
   a needle tip at said distal end of said barrel;
   a basically cylindrical, plunger rod extending beyond said barrel and having a longitudinal axis located within said barrel for axial movement therein for drawing fluid into and expelling fluid out of said barrel through said needle tip, said plunger rod having at least one ratchet tooth and also having a barrel sidewall-scaling piston at its distal end near said needle tip end of said barrel, said plunger rod comprising an aspirating gap comprising a smooth wall of reduced diameter of said plunger rod with respect to said ratchet tooth, said aspirating gap being proximally located with respect to said ratchet tooth;
   a radially, resilient, open-walled spring locking clip initially mounted about said aspirating gap of said plunger rod, said spring locking clip having ratchet tooth-engaging means and at least one, outwardly-directed locking barb having a sidewall contact point, said spring locking clip being forced to move distally along with said plunger rod after said plunger rod is first moved sufficiently proximally with respect to said barrel and said spring locking clip such that said tooth engaging means of said spring locking clip mechanically engages said ratchet tooth of said plunger rod;
   said plunger rod being free to reciprocate for aspiration when said spring locking clip is located on said aspirating gap of said plunger rod, said locking spring clip being held in position within said barrel by the frictional digging of said contact point into said sidewall as said plunger rod moves proximally and distally but the latter only while said spring locking clip is located about said aspirating gap and prior to mechanical engagement of said spring locking clip with said ratchet tooth, and, thus distal movement of said plunger rod, after sufficient proximal movement of said plunger rod such that said spring locking clip is mechanically engaged with said ratchet tooth, causes distal movement of said spring locking clip by mechanical interconnection of said ratchet tooth-engaging means with said spring locking clip;
      whereby aspiration can be accomplished and said spring locking clip and plunger rod permit the syringe to be loaded with medication in the volume of said barrel defined by a predetermined location of said spring looking clip on said plunger rod by proximal movement of said plunger, and, after mechanical engagement between said spring locking clip and said ratchet tooth, distal movement of said plunger rod expels said medication and distally moves said spring locking clip within said barrel such that said plunger rod is prevented from a second full barrel length movement by said piston abutting said spring locking clip such that frictional digging in between said contact point and said interior cylindrical sidewall results.

2. A single-use syringe as claimed in claim 1 wherein said plunger rod ratchet tooth engaging means comprises an inwardly directed contact element.

3. A single-use syringe as claimed in claim 1 wherein said spring locking clip extends around said plunger rod in the range of about 180° to less than 360°.

4. A single-use syringe as claimed in claim 1 wherein said spring locking clip extends less than about 180° around said plunger rod.

5. A single-use syringe as claimed in claim 1 wherein said spring locking clip extends less than 180° and more than about 27° around said plunger rod.

6. A single-use syringe as claimed in claim 1 wherein the medication-containing volume of said barrel is defined by initial position of said spring locking clip on said plunger rod and is as low as about 0.1 cc.

7. A single-use syringe as claimed in claim 1 wherein said spring locking clip deflects said plunger rod, during movement, out of axial alignment with respect to the axis of said hollow barrel.

8. A single-use syringe as claimed in claim 1, wherein each of said ratchet teeth is frusto-conical.

9. A single-use syringe as claimed in claim 1 wherein each of said ratchet teeth is bead-like.

10. A single-use syringe as claimed in claim 1 wherein sealing means are provided at both the distal end and the proximal end of said plunger rod to provide a sterile chamber for medication and to prevent unauthorized access to said spring locking clip.

11. A single-use syringe as claimed in claim 1 wherein said plunger rod is provided with at least one fracture plane having a tensile strength less than the frictional resistance between said contact point of said spring locking clip and said sidewall of said barrel.

12. A single-use syringe as claimed in claim 1 wherein said plunger rod is provided with two or more axially spaced aspirating gaps and at least one ratchet tooth is provided distally located with respect to each of said aspirating gaps.

13. A single-use syringe as claimed in claim 1 wherein said ratchet tooth engaging means flexes radially outwardly over the surface of each of said ratchet teeth as said plunger rod moves proximally thereover.

14. A single-use syringe as claimed in claim 1 wherein said ratchet tooth engaging means, when engaged at base of said ratchet tooth, will move with said plunger rod when said plunger rod is moved distally.

15. A single use syringe as claimed in claim 1, wherein said aspirating gap comprises a section of said plunger rod of diameter smaller than each of said ratchet teeth.

16. A single use syringe as claimed in claim 1, wherein two or more aspirating gaps are provided to said plunger rod, each of said gaps being located between adjacent ratchet teeth of said plunger rod.

17. A single use syringe as claimed in claim 16, wherein said aspirating gaps are of unequal length.

18. A single use syringe as claimed in claim 1, wherein said aspirating gap is disabled by proximal movement of said plunger rod to an extent that said spring locking clip becomes mechanically linked to said ratchet tooth of said plunger rod.

19. A single use syringe as claimed in claim 16, wherein said aspirating gaps are sequentially disabled by each proximal movement of said plunger rod to an extent that said spring locking clip becomes mechanically linked to a ratchet tooth of said plunger rod adjacent said aspirating gap.

* * * * *